United States Patent [19]
Golosarsky et al.

[11] Patent Number: 5,891,044
[45] Date of Patent: *Apr. 6, 1999

[54] DETECTION OF ABNORMAL AND INDUCTION OF NORMAL HEART RATE VARIABILITY

[75] Inventors: Boris Golosarsky, Cincinnati, Ohio; Nicholas Wood, Rowayton, Conn.

[73] Assignee: GW Scientific, Inc., Rowayton, Conn.

[*] Notice: The term of this patent shall not extend beyond the expiration date of Pat. No. 5,718,235.

[21] Appl. No.: 781,330

[22] Filed: Jan. 10, 1997

Related U.S. Application Data

[63] Continuation of PCT/US95/08943 Jul. 13, 1995 which is a continuation of Ser. No. 482,980, Jun. 7, 1995, abandoned, which is a continuation of Ser. No. 274,321, Jul. 13, 1994, abandoned, which is a continuation-in-part of Ser. No. 689,144, Jul. 30, 1996, Pat. No. 5,718,235, Ser. No. 482,980, and Ser. No. 274,321, and a continuation of Ser. No. 957,611, Oct. 6, 1992, abandoned.

[51] Int. Cl.⁶ .................................................. A61B 5/0456
[52] U.S. Cl. ............................................................ 600/509
[58] Field of Search .................................. 128/696, 697, 128/702, 704, 705, 708, 903, 904; 607/14, 17, 27; 600/509, 510, 515, 517, 518, 521

[56] References Cited

U.S. PATENT DOCUMENTS

| D. 278,746 | 5/1985 | Saynajakangas . | |
|---|---|---|---|
| D. 287,403 | 12/1986 | Kiiski et al. . | |
| 4,018,219 | 4/1977 | Hojaiban . | |
| 4,312,356 | 1/1982 | Sowton et al. | 607/14 |
| 4,453,537 | 6/1984 | Spitzer . | |
| 4,531,527 | 7/1985 | Reinhold, Jr. et al. | 128/696 |
| 4,572,192 | 2/1986 | Jackman et al. . | |
| 4,625,733 | 12/1986 | Säynäjäkangas . | |
| 4,883,063 | 11/1989 | Bernard et al. . | |
| 4,960,129 | 10/1990 | dePaola et al. . | |
| 5,042,497 | 8/1991 | Shapland . | |

(List continued on next page.)

FOREIGN PATENT DOCUMENTS

| 1607808A1 | 11/1990 | U.S.S.R. . |
|---|---|---|
| 1683679A1 | 10/1991 | U.S.S.R. . |
| 1769894A1 | 10/1992 | U.S.S.R. . |

OTHER PUBLICATIONS

Malik, Farrell, Cripps, Camm, Heart Rate Variability in Relation to Prognosis After Myocardial Infarction: Selection of Optimal Processing Techniques. *Eur. Heart J.* 1989; 10:1060–1074.

Malik, Xia, Odeuyiwa, Stauton, Polonieki, Camm, Influence of the Recognition Artefact in the Automatic Analysis of Long–term Electrocardiograms on Time–domain Measurement of Heart rate Variability, *Med. Biol. Eng. Comput.* 1993; 31:539–544.

Malik, Camm, Components of Heart Rate Variability: What They Really Mean and What We Really Measure, *Am. J. Cardiol.* 1993; 72:821–822.

Malik, Cripps, Farrell, Camm,. Prognostic Value of Heart Rate Variability After Myocardial Infraction: A Comparison of Different Data Processing Methods, *Med. Biol. Eng. Comput.* 1989;27:603–611.

(List continued on next page.)

*Primary Examiner*—George Manuel
*Attorney, Agent, or Firm*—Stevens, Davis, Miller & Mosher, L.L.P.

[57] ABSTRACT

A microprocessor (300) with a date and time clock gathers time interval data (80, 86). The duration of the time intervals in an electrocardiogram, or pulses are recorded. Stress data accumulated for the user are down loaded to a PC (301). The battery power pack (303) supplies electricity to operate the components (80–318). The user's stress status is displayed on a liquid crystal diode (302), and the voice microprocessor (318) broadcasts from a microspeaker CPR instructions. If the battery (303) has less than a 20% charge, a buzzer (304) notifies the user.

34 Claims, 28 Drawing Sheets

U.S. PATENT DOCUMENTS

| | | |
|---|---|---|
| 5,058,597 | 10/1991 | Onoda et al. . |
| 5,078,133 | 1/1992 | Heinz et al. ............................. 607/17 |
| 5,265,617 | 11/1993 | Verrier et al. . |
| 5,419,338 | 5/1995 | Sarma et al. . |
| 5,437,285 | 8/1995 | Verrier et al. . |
| 5,462,060 | 10/1995 | Jacobson et al. ........................ 128/702 |
| 5,522,854 | 6/1996 | Ideker et al. . |
| 5,560,368 | 10/1996 | Berger . |
| 5,560,370 | 10/1996 | Verrier et al. . |

OTHER PUBLICATIONS

Malik, Camm, Heart Rate Variability and Clinical Cardiology, *Br. Heart J.* 1994; 71:3–6.

Malik, Camm. Significance of Long–term components of Heart Rate Variability for the Further Prognosis After Acute Myocardiol Infarction, *Cardiovasc. Res.* 1990;24:793–803.

Fei, Malik, Short– and long–term Assessment of Heart Rate Variability for Postinfarction Risk Stratification, In: Malik, Camm, eds, *Heart Rate Variability*, Armonk, Ny: Futura; 1995: 341–346.

Heart Rate Variability Standards of Measurement, Physiological Interpretation, and Claincal Use, Circulation, Vol. 93, No. 5, (Mar. 1, 1996.)

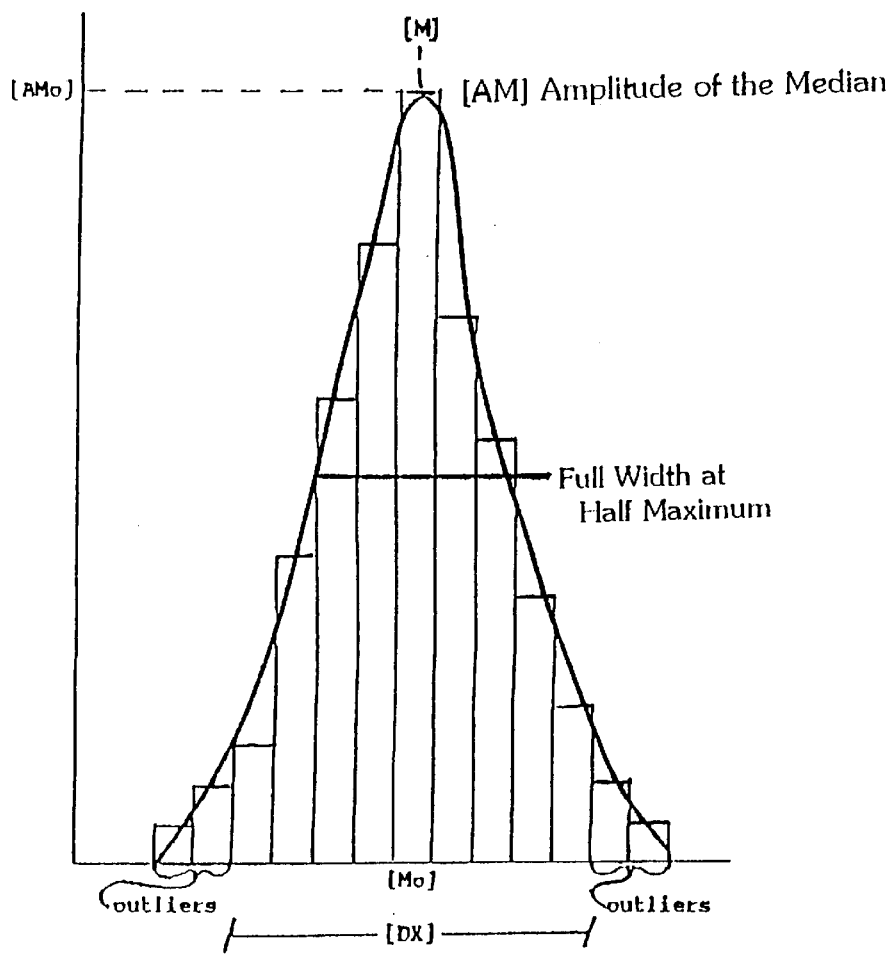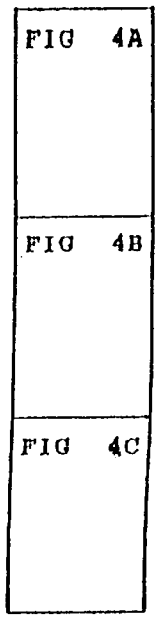

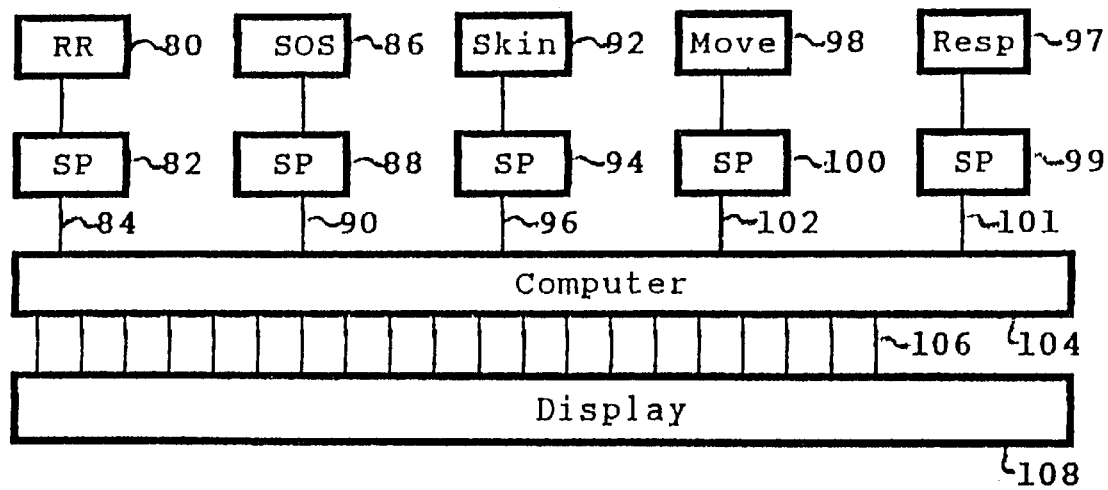
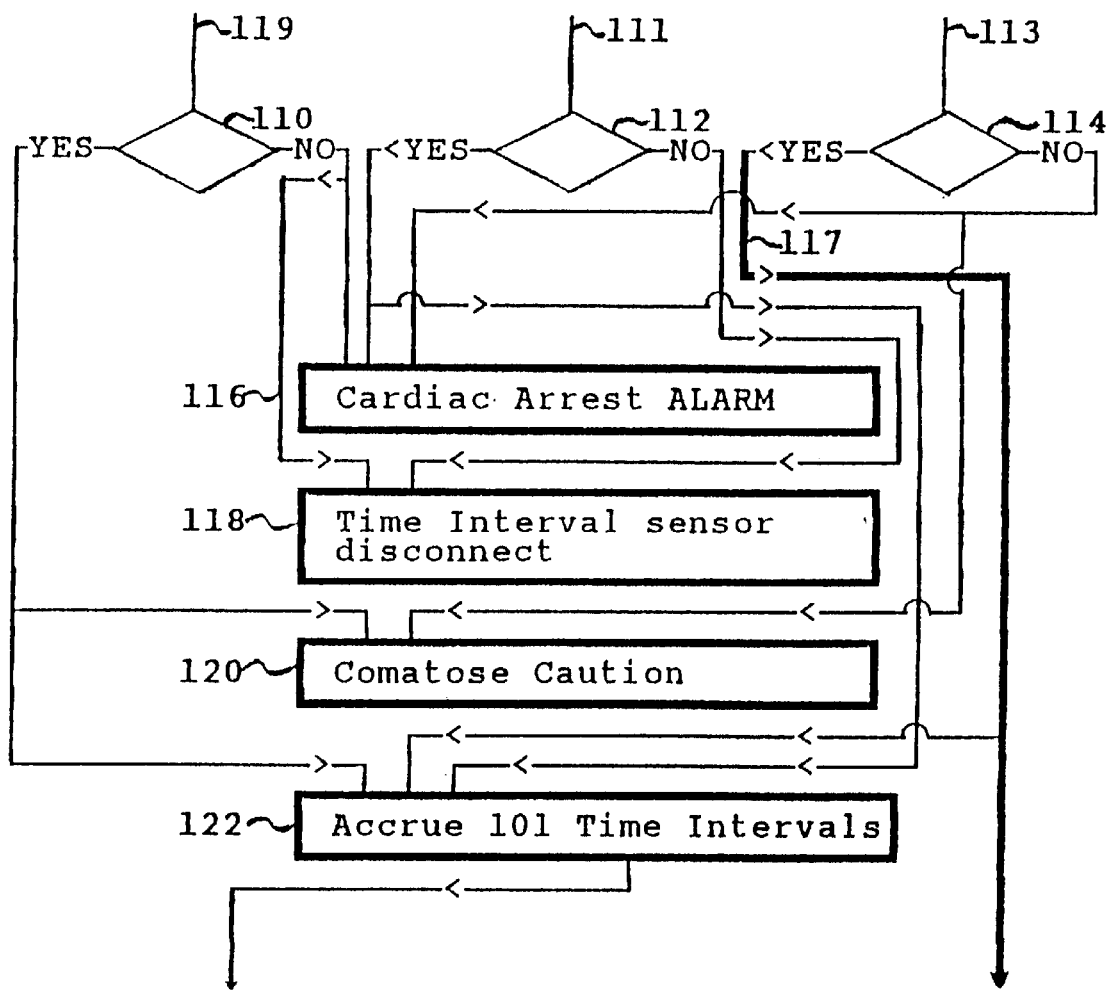

FIG 8

| Patient | Room | UV | AMo | DX | PVC | BPM | Status UV | AMo | DX | ALARM Set | ALARM Duration |
|---|---|---|---|---|---|---|---|---|---|---|---|
| Patient 1 | 812A | 6.7 | 35 | .12 | 0 | 78 | OK | OK | OK | 30 | 0 |
| Patient 2 | 805B | 13.1 | 45 | .08 | 1 | 85 | S | S | OK | 30 | 6 |
| Patient 3 | 810A | 13.5 | 44 | .08 | 5 | 88 | P | OK | P | 30 | 3 |
| Patient 4 | 801B | 7.2 | 42 | .10 | 0 | 81 | OK | OK | OK | 30 | 0 |
| Patient 5 | 814A | 7.5 | 36 | .12 | 0 | 75 | OK | OK | OK | 30 | 0 |
| Patient 6 | 809B | 8.5 | 37 | .12 | 0 | 72 | OK | OK | OK | 30 | 0 |
| Patient 7 | 802B | 3.2 | 21 | .18 | 0 | 96 | OK | P | OK | 30 | 27 |
| Patient 8 | 802A | 40.1 | 80 | .06 | 7 | 102 | S | S | S | 30 | 31 |

Date:12/01/94    Time:18:02    GWS

FIG 9

| Patient | Room | UV | AMo | DX | PVC | BPM | ALARM Set | ALARM Duration |
|---|---|---|---|---|---|---|---|---|
| Patient 8 | 802A | S40.1 | S80 | S.06 | 7 | 102 | 30 | 31 |
| ALARM Settings | | S42.3 | S81 | S.06 | 8 | 101 | " | 29 |
| Base — MF — ALARM | | | | | | | | |
| SUV  1.2   22.8 | | S43.2 | S80 | S.06 | 9 | 97 | " | 27 |
| PUV  .85   16.2 | | | | | | | | |
| SAMo 1.1   61 | | S40.2 | S81 | S.06 | 5 | 98 | " | 26 |
| PAMo .85   47 | | | | | | | | |
| SDX  .85  .06 | | S40.4 | S79 | S.06 | 6 | 99 | " | 24 |
| PDX  1.15 .10 | | | | | | | | |
| PVCs avg pre 8  20%+ | | S41.5 | S79 | S.06 | 1 | 102 | " | 22 |
| DX ≥       .50 | | | | | | | | |
| AMo≤      10 | | S40.4 | S78 | S.06 | 3 | 95 | " | 20 |
| DX/M≥     .425 | | | | | | | | |
| DX/M≤     .125 | | S44.5 | S77 | S.04 | 0 | 96 | " | 19 |
| ALARM Durations | | S44.3 | S76 | S.04 | 0 | 105 | " | 18 |
| — ALARM — If for — | | | | | | | | |
| SUV     30 min | | S40.3 | S80 | S.06 | 0 | 101 | " | 16 |
| PUV     30 min | | | | | | | | |
| SAMo    30 min | | S39.2 | S82 | S.06 | 0 | 97 | " | 14 |
| PAMo    30 min | | | | | | | | |
| SDX     30 min | | S38.8 | S83 | S.06 | 0 | 97 | " | 12 |
| PDX     30 min | | | | | | | | |
| PVC's   30 min | | S37.6 | S85 | S.06 | 0 | 99 | " | 11 |
| DX       2/10 | | | | | | | | |
| AMo      2/10 | | S35.8 | S86 | S.08 | 0 | 103 | " | 9 |
| DX/M     2/10 | | | | | | | | |
| DX/M     2/10 | | S35.2 | S84 | S.08 | 0 | 101 | " | 7 |

Baseline Data 8:00-10:00 11/29/94 ⌀12/01/94 Time:18:02 GWS

FIG 49A

Recorded Modes
1st Cluster Mode measured in seconds

|     | Mo1  | Mo2  | Mo3  |
|-----|------|------|------|
| UV  | UV1  | UV2  | UV3  |
| AMo | AMo1 | AMo2 | AMo3 |
| DX  | DX1  | DX2  | DX3  |

FIG 49B

Recorded Modes        Recorded Modes
1st Cluster Mode      2nd Cluster Mode measured in seconds

|     | Mo1  | Mo2  | Mo3  | Mo4  | Mo5  | Mo6  |
|-----|------|------|------|------|------|------|
| UV  | UV1  | UV2  | UV3  | UV4  | UV5  | UV6  |
| AMo | AMo1 | AMo2 | AMo3 | AMo4 | AMo5 | AMo6 |
| DX  | DX1  | DX2  | DX3  | DX4  | DX5  | DX6  |

FIG 49C

Inferred Modes         Recorded Modes        Recorded Modes
3rd Cluster Mode       1st Cluster Mode      2nd Cluster Mode measured in seconds

|     | Mo7  | Mo8  | Mo9  | Mo1  | Mo2  | Mo3  | Mo4  | Mo5  | Mo6  |
|-----|------|------|------|------|------|------|------|------|------|
| UV  | UV7  | UV8  | UV9  | UV1  | UV2  | UV3  | UV4  | UV5  | UV6  |
| AMo | AMo7 | AMo8 | AMo9 | AMo1 | AMo2 | AMo3 | AMo4 | AMo5 | AMo6 |
| DX  | DX7  | DX8  | DX9  | DX1  | DX2  | DX3  | DX4  | DX5  | DX6  |

FIG 49D

| | Inferred Modes | Recorded Modes | Recorded Modes |
|---|---|---|---|
| | | measured in seconds | |
| Avgs | 3rd Cluster Mode | 1st Cluster Mode | 2nd Cluster Mode |
| UV | Fr UV7 to UV9 | Fr UV1 to UV3 | Fr UV4 to UV6 |
| AMo | Fr AMo7 to AMo9 | Fr AMo1 to AMo3 | Fr AMo4 to AMo6 |
| DX | Fr DX7 to DX9 | Fr DX1 to DX3 | Fr DX4 to DX6 |

FIG 49E

| | Inferred Modes | Recorded Modes | Recorded Modes |
|---|---|---|---|
| | | measured in seconds | |
| ALARM Levels | 3rd Cluster Mode | 1st Cluster Mode | 2nd Cluster Mode |
| UV | *1.15=SUV<br>Fr UV 7 to 9<br>* .85=PUV | *1.15=SUV<br>Fr UV 1 to 3<br>* .85=PUV | *1.15=SUV<br>FR UV 4 to 6<br>* .85=PUV |
| AMo | *1.10=SAMo<br>AMo7 to 9<br>* .90=PAMo | *1.10=SAMo<br>AMo 1 to 3<br>* .90=PAMo | *1.10=SAMo<br>AMo 4 to 6<br>* .90=PAMo |
| DX | * .90=SDX<br>DX 7 to 9<br>*1.10=PDX | * .90=SDX<br>DX 1 to 3<br>*1.10=PDX | * .90=SDX<br>DX 4 to 6<br>*1.10=PDX |

FIG 50

HEALTHY Male    AMo=27    DX=.16

| secs | bpm | histogram | Num |
|---|---|---|---|
| .64 | 94 | x | 1 |
| .66 | 91 | x x | 4 |
| .68 | 88 | xx xx   x xx | 15 |
| .70 | 86 | x   x xx  xx x  x | 12 |
| .72 | 83 | x  xx xx xx | 6 |
| .74 | 81 | x  x | 4 |
| .76 | 79 | xxx   x xx x xxx | 13 |
| .78 | 77 | xxx  xx xx x xx1 xxx xxl x xxx | 27 |
| .80 | 75 | xx xx1 x xx x xx | 15 |
| .82 | 73 | x  x | 2 |
| .84 | 71 |  |  |
|  |  |  | 101 |

Time ———→

FIG 51

UNHEALTHY Male    AMo=52    DX=.04

| secs | bpm | histogram | Num |
|---|---|---|---|
| .64 | 94 |  |  |
| .66 | 91 |  |  |
| .68 | 88 |  |  |
| .70 | 86 |  |  |
| .72 | 83 |  |  |
| .74 | 81 | x | 20 |
| .76 | 79 | xxxxxxxx  x   xxxxxxxxxx | 52 |
| .78 | 77 | xxxxxxxxxxxxxxxxxxxxxxxxxxx xxx xx | 29 |
| .80 | 75 | xx x x xx xxxx xx | |
| .82 | 73 | x x | |
| .84 | 71 |  |  |
|  |  |  | 101 |

Time ———→

DETECTION OF ABNORMAL AND INDUCTION OF NORMAL HEART RATE VARIABILITY

RELATED APPLICATIONS

This application is a continuation of PCT patent application Ser. No. PCT/US95/08943 to Golosarsky et al filed Jul. 13, 1995, which is a continuation and claims priority from U.S. patent application Ser. No. 08/482,980 to Golosarsky et al, filed Jun. 7, 1995 now abandoned, which is a continuation-in-part of U.S. patent application Ser. No. 08/274,321 to Golosarsky et al, filed Jul. 13, 1994 now abandoned.

This application is also a continuation-in-part of U.S. patent application Ser. No. 08/689,144 to Golosarsky et al filed Jul. 30, 1996 now U.S. Pat. No. 5,718,235 which is a continuation of U.S. Pat. application Ser. No. 08/482,980 to Golosarsky et al filed Jun. 7, 1995 now abandoned, which is a continuation-in-part of U.S. Patent application Ser. No. 08/274,321 to Golosarsky et al filed Jul. 13, 1994 now abandoned, which is a continuation of U.S. patent application Ser. No. 07/957,611 to Golosarsky filed Oct. 6, 1992 now abandoned. Said applications are incorporated herein by reference in their entirety.

TECHNICAL FIELD

This invention relates to the detection of normal and abnormal heart rate variability and the induction of normal heart rate variability. More particularly, the invention relates to methods and apparatus for the detection of a user's heart rate variability that we believe is indicative of a user's sympathetic/parasympathetic stress balance, or distress imbalance.

The invention also relates to heart monitoring devices used by individuals monitored in hospital intensive care units; by user's after discharge from a hospital intensive care unit; and by users when exercising to let them know that their stress state is optimal for conditioning their bodies.

The invention further relates to control of a pacemaker or cardioverter defibrillator with a pacemaker so that when the user's heart rate is abnormal and distressful, according to the invention, a pacemaker or cardioverter defibrillator with a pacemaker induces a heart rate with a pseudo-normal or patient recorded variability for each particular user.

The invention still further relates to a pacemaker that induces pseudo-normal or patient recorded heart rate variability.

BACKGROUND ART

The normal heart rhythm is slightly irregular. Generally, normal irregularity of the heart's rhythm reflects the permanent adaptation of the human body to the environment. In this context the first sign of an impaired heart rhythm is either a persistent increase or a persistent decrease in the variability of the heart's rhythm. Sometimes the change in the heart's rhythm alternates between increases and decreases in the variability of the heart's rhythm, and vice versa. Prolonged increases, or decreases, and combinations thereof, can lead to cardiac ectopic events ranging from non-sustained ventricular tachycardia to cardiac arrest.

It is believed the variability of the heart's rhythm is controlled by two branches of the autonomic nervous system; the sympathetic branch and the parasympathetic branch. The sympathetic branch increases the heart rate. Its prime function is to prepare the body for stress, the so-called "fight or flight response". The parasympathetic branch decreases the heart rate as when eating or sleeping.

In the Soviet Union, Rhythmography, that is the study of normal and abnormal variations in heart rhythm, was utilized extensively to determine the condition of individuals and their stress state. This was particularly true of cosmonauts. It was determined for example, that the heart rate variability of a conditioned athlete is much greater than that of person with coronary disease, that is the histogram of heart rate variation of a well conditioned athlete exhibits a broad range of variability in the Time Intervals between heart beats and a low relative Amplitude of the Mode. That is the highest number of Time Intervals recorded in a series of Time Intervals. The histogram of a person with a coronary disease exhibits a narrow range of variability and a high relative Amplitude of the Mode, that is the peak of the histogram.

Applicant, Boris Golosarsky, previously received two patents in the Soviet Union, namely; SU-1683679 for an apparatus, which enables a physician to determine the arithmetic Mean, the Mode, the relative Amplitude of the Mode, and the range of variability of a subject. In the second patent in the Soviet Union, SU-1769894, he disclosed how these measurements may be utilized together with electrosleep to treat post myocardial infarction e.g. heart attack patients.

Polar Electro Oy of Finland has a patented apparatus comprised of a chest strap with a two lead ECO signal sensor and transmitter, which transmits the heart beat Time Intervals to a wrist mounted unit that can be conveniently used in this invention. See U.S. Pat. Nos. 4,625,733, D278,746, and D287,403.

Pulse sensors of various types may also be used to detect the Time Interval between heart beats, (Start-of-Systole to Start-of-Systole, SOS), is essentially equal to the Time Interval between RR peaks in an electrocardiogram, (ECG).

DISCLOSURE OF THE INVENTION

DEFINITIONS

Data sources: ECG (RR) Time Intervals or pulse wave Start-of-Systole to Start-of-Systole (SOS) Time Intervals from the hardware sources discussed elsewhere. (Note: RR and SOS Time Intervals are used interchangeably to indicate the Time Interval between heart beats. 60 seconds divided by the Time Interval in seconds equals the beats per minute.)

Time Interval: A Time Interval is the duration of time between heart beats, preferably measured to an accuracy of 20 milliseconds, 0.02 seconds. The accuracy of the Time Interval can range from 15 milliseconds to 30 milliseconds.

Time Segment: A Time Segment is a series of heart beats can vary in length from 51 Time Intervals to 301 Time Intervals. The preferred default setting is 101 Time Intervals.

Mode, [Mo]: The Mode is the Time Interval occurring most often in a Time Segment. For each Mode in a Time Segment there are recorded values for UV, AMo, and DX. (See below).

Cluster Mode: A Cluster Mode is a group of Modes occurring in a plurality of adjoining successive Time Segments. For each Cluster Mode there are recorded values for UV, AMo, and DX. (See below).

Amplitude of the Mode, [AMo]: The Amplitude of the Mode is the largest number of identical Time Intervals occurring in a Time Segment divided by the total number of Time Intervals in said Time Segment, which is expressed as a percentage. (e.g. 70 for 70 Time Intervals out of 101 Time Intervals.)

Delta X, [Dx]: Delta X is the difference between the longest value for a Time Interval in a Time Segment and the shortest value, after outliers, (see below) and Premature Ventricular Contractions, (PVC's) (see below), if any, have been discarded. (e.g. longest equals 0.72 seconds less shortest equals 0.64 seconds=0.08 second=Delta x.)
User Value is determined by the formula $$UV = \sqrt{[.5/DX]^2 + [AMo/10]^2}$$

Median [M]: The Median is the Time Interval in a Time Segment, in which there are equal number Time Intervals equal to or larger than and equal to or smaller than the Median Time Interval (e.g. the 51st Time Interval in a 101 Time Interval Time Segment.)

Time Interval, Recorded: The user's recorded Time Interval is the Time Interval between two ECG (RR) peaks, or pulse wave Start of Systole to Start of Systole, (SOS) troughs recorded by the user.

Time Interval, Inferred: An inferred Time Interval is an a Time Interval that is inferred from recorded or other inferred Time Intervals.

Recorded Baseline UV, AMo, and DX The Recorded Baseline values for UV, AMo, & DX are established during the first period monitoring the user. Preferably this a 24 hour time period, but could be shortened when required, e.g. in an emergency room. The Recorded Baseline values should be re-recorded every year. As people age their heart rhythm tends to become less variable.

Recorded and Inferred Baseline UV, AMo, & DX If time does not permit recording the first 24 hours of UV, AMo, & DX, then at least 35 Time Segments are recorded and the first five Time Segments are discarded since they are part of the calibration and run-in period. The minimum acceptable recorded values for UV, AMO and DX are for three successively occurring Modes, which creates one Cluster Mode.

Premature Ventricular Contractions, [PVC's] A PVC is a Time Interval that is 20% less than the average of the previous eight Time Intervals. PVC's are discarded and new Time Intervals added until 101 Time Intervals are accumulated in a Time Segment.

Outliers are the three shortest and the three longest Time Intervals in a 101 beat Time Segment, and are discarded before calculations are made for UV, AMo and DX.

Normalized Baseline Values UV, AMo, & DX, If the user's Recorded Baseline Values for UV, AMo, & DX are judged to be abnormal, then the variable heart rhythm of an individual most nearly matching the user's age, sex, race, build and athletic condition is substituted.

User A user is anyone whose Time Intervals are recorded.
OK: The user's physical condition is normal and not stressed.
Caution: The user has a potentially unhealthy stress condition.

ALARM 1 is present when the user's current values for UV, AMo or DX indicate sympathetic, parasympathetic, mixed sympathetic/parasympathetic over activity, or PVC's, for a predetermined number of Time Segments or a predetermined period of time.

ALARM 2 is present when no pulse is detected for ten or more seconds and the galvanic,skin response sensor indicates the ECC electrodes or the pulse sensor is in contact with the user.

Motion Sensor

A transducer detects a range of motions from, no motion, to slight motion, to moderate motion to heavy motion and over load.

No motion for a predetermined period of time and a heart or pulse rate indicates a Comatose Caution. Slight motion and a heart or pulse rate indicate sleep. Heavy motion indicates exercise and over load (spike) followed by no motion, indicates a fall.

The invention provides for the automatic detection of the user's functional and stress states based on the on-line recording of the Median, [M], one or more Cluster Modes, [CMo], the Amplitude of the Mode, [AMo], and Delta X, [DX], and User Value, [UV], recorded over successive Time Segments.

19 formulas are used to determine the user's stress status and possible ALARM, Caution, and normal OK stress condition. The multiplier factors and time durations of the 19 formulas are programmable by the user's health care provider to suit the individual user.

Cardiac Arrest ALARM

If no Time Intervals are detected for 15 or more seconds and the galvanic skin response sensor indicates the ECG electrodes or the pulse sensor is in contact with the user, then this is a Cardiac Arrest ALARM.

Comatose Caution

If Time Intervals are detected but no motion is detected for 30 or more minutes, then this is a Comatose Caution.

PVC ALARM

[1] If a Time Interval differs from the average of the previous eight Time Intervals by 20% or more, 20 or more times in a single 101 Time Interval Time Segment, for 10 minutes or longer, then this is a PVC ALARM.

AMo Sympathetic ALARM

[2] If the current value for AMo is greater than the user's baseline value for AMo for any Cluster Made, times a predetermined multiplier factor for a predetermined number of minutes, then this is an AMo Sympathetic ALARM.

AMo Parasympathetic ALARM

[3] If the current value for AMo is lesser than the user's baseline value for AMo for any Cluster Mode, times a predetermined multiplier factor for a predetermined number of minutes, then this is an AMo Parasympathetic ALARM.

DX Sympathetic ALARM

[4] If the current value for DX is lesser than the user's baseline value for DX for any Cluster Mode, times a predetermined multiplier factor for a predetermined number of minutes, then this is an DX Sympathetic ALARM.

DX Parasympathetic ALARM

[5] If the current value for DX is greater than the user's baseline value for DX for any Cluster Mode, times a predetermined multiplier factor for a predetermined number of minutes, then this is an DX Parasympathetic ALARM.

Mixed Sympathetic/Parasympathetic ALARM-Long Term

[6] Any combination of a Sympathetic ALARM, [2], and Parasympathetic ALARM, [3], for a predetermined number of minutes is a Mixed Sympathetic/Parasympathetic ALARM-Long Term.

Mixed Sympathetic/Parasympathetic ALARM-Short Term

[7] Any combination of a Sympathetic ALARM, [2][4], and a Parasympathetic ALARM, [3][5] in 101 Time Interval Time Segment, in two or more times in any continuous grouping of ten Time Segments is a Mixed Sympathetic/Parasympathetic ALARM-Short Term.

UV Sympathetic ALARM

[8] If the current value for UV is greater than the user's baseline value for UV for any Cluster Mode, times a predetermined multiplier factor for a predetermined number of minutes, then this is a UV Sympathetic ALARM.

UV Parasympathetic ALARM

[9] If the current value for UV is lesser than the user's baseline value for UV for any Cluster Mode, times a predetermined multiplier factor for a predetermined number of minutes, then this is an UV Parasympathetic ALARM.

UV Mixed Sympathetic/Parasympathetic ALARM-Long Term

[10] Any combination of a UV Sympathetic ALARM, [8], and a UV Parasympathetic ALARM, [9], for a predetermined number of minutes is a UV Mixed Sympathetic/Parasympathetic ALARM-Long Term.

UV Mixed Sympathetic/Parasympathetic ALARM-Short Term [11] Any combination of a UV Sympathetic ALARM, [8], and a UV Parasympathetic ALARM, [9] in 101 Time Interval Time Segment, in two or more times in any continuous grouping of ten Time Segments is a UV Mixed Sympathetic/Parasympathetic ALARM-Short Term.

The Cardiac Arrest ALARM, Comatose Caution, and the PVC ALARM and the next six formulas for ALARMS and Cautions are absolute, and not dependant on the user's baseline values.

Sympathetic ALARM-Type II

[12] If DX divided by the Median is equal or less than 0.125, and in two or more times in any continuous grouping of ten Time Segments, then this is a Sympathetic ALARM-Type II.

Parasympathetic ALARM-Type II

[13] if DX divided by the Median is equal or greater than 0.425, in two or more times in any continuous group of ten Time Segments, then this is a Parasympathetic ALARM-Type II.

Parasympathetic ALARM-Type III

[14] If DX is equal or greater than 0.50 in two or more Time Segments in any continuous group of ten Time Segments, then this is Parasympathetic ALARM-Type III.

Parasympathetic ALARM-Type IV

[15] If AMo is equal or less than 10 in two or more Time Segments in any continuous grouping of ten Time Segments, then this is a Parasympathetic ALARM-Type IV.

Sympathetic Caution-Long Term

[16] If DX equals 0.06 or less for one hour or longer, then this is a Sympathetic Caution-Long Term.

Caution-Short Term

[17] If AMo and DX vary directly with each other in a single or adjoining Cluster Modes for one hour or longer, then this is a Caution-Short Term.

If the Median and the Mode differ from each other in a 101 Time Interval Time Segment by 20% or more, than this a case of non-stationarity and the values generated are discarded and not included in calculations.

It is believed that other formulas characterizing the histogram might be used after further analysis of the data. These could be the width at half maximum of the histogram instead of DX, the use of Standard Deviation instead of DX, and the Amplitude of the Median instead of AMo in the 17 formulas where applicable.

The user's functional and stress states may be displayed to the user or a health care provider in an alphanumeric fashion. This enables the user or health care provider to determine the user's stress status substantially instantaneously at any time or place, and to attain a state of effective cardiovascular fitness.

The inventors believe that the triangle of the histogram indicated by formulas [8] and [9], e.g. the sharpness, or flatness of the histogram, (is equivalent to the Q of a resonant circuit), is a measure for each Cluster Mode that indicates that the user is in a normal autonomic balance or homeostasis between sympathetic and parasympathetic control of the user's heart rate variability.

Abnormal deviation of these functions above or below those recorded in both healthy and unhealthy subjects indicate abnormal stress and thus cardiac distress.

Detection of abnormal heart rate variability in a series of Time Segments can therefore be used to signal a health care provider, or pacemaker, or cardioverter defibrillator with a pace maker, to intervene according to the invention, or to indicate that the heart is being over stressed by the particular activity (e.g. physical, psychogenic) being engaged in.

Also according to the invention, a pacemaker or a cardioverter defibrillator with a pacemaker can be programmed to provide a normal, therapeutic heart rate variability rather than an unnatural steady beat as in the prior art. This may be accomplished by, (1) recording the user's normal, variable heart rate, or (2) the normal, variable heart rhythm of an individual most nearly matching the user's age, sex, race, build and athletic condition, or (3) using a random pulse generator that produces a normal, variable histographic heart rate, all in conjunction with an impedance pacemaker, (a pacemaker that detects respiration) and a galvanic skin response detector.

OBJECTS OF THE INVENTION

It is the therefore an object of this invention to provide a method and apparatus for determining the user's stress state.

Another object of the invention is to provide such apparatus, which allows the user to exercise in a stress state which will bring about a maximum conditioning effect.

A further object of the invention is to provide such apparatus and method that the user will be notified of non-optimal or an ALARM or Caution distress state.

Still another object of the invention is to detect stress and distress states from simple parameters derived from the recording of a plurality of durations of successive Time Intervals between heart beats.

Yet another object of the invention is to detect cardiac distress.

Still another object of the invention is to detect abnormal heart rate variability over a relatively short period of time and to signal this abnormality to a health care provider, or a pacemaker or a cardioverter defibrillator with a pacemaker, to initiate intervention.

A still further object of the invention is to cause a pacemaker or cardioverter defibrillator with a pacemaker, to pace a heart with a normal heart rate variability.

Other objects of the invention will in part be obvious and will in part appear hereinafter.

The invention accordingly comprises a method comprising several steps and the relation of one or more of such steps with respect to each of the others, and the apparatus embodying features of construction, elements, and arrangements of parts, which are adapted to effect such steps, all as exemplified in the following detailed disclosure.

The scope of the invention will be indicated in the claims.

For a fuller understanding of the nature and objects of the invention, reference should be had to the following detailed description taken in connection with the drawings forming a part thereof.

SUMMARY OF THE INVENTION

The present invention provides a method of detecting abnormal heart rate variability comprising:

A) first recording a first subject's instantaneous heart rate or RR intervals over substantially no less than 50 to substantially no more than 300 heart beat segments occurring with normal heart rate variability;

B) characterizing the sharpness of histograms of said segments comprising the numbers of each of the heart rate or RR intervals recorded versus each particular heart rate or RR interval as a function of the Mode of each of the segments;

C) second recording a second subject's heart rate or RR intervals over substantially no less than 50 to substantially no more than 300 heart beat segments;

D) characterizing the sharpness of the histograms of the second subject's heart rate or RR interval variations as a function of the Mode of each of the segments; and E) indicating when the sharpness of the histograms of the second subject deviates from predetermined limits derived from the histograms of the first subject.

The sharpness may be characterized by the Amplitude of the Mode (AMo) occurring in the segment. The sharpness may also be characterized by a number proportional to the ratio of the Amplitude of the mode (AMo) expressed as a percentage to the difference between substantially the largest and substantially the smallest instantaneous heart rate or RR interval in a segment (DX).

The method of the present invention may also include characterizing sharpness by a number proportional to the ratio of the Amplitude of the mode (AMo) expressed as a percentage to the difference between substantially the largest and substantially the smallest instantaneous heart rate or RR interval in a segment (DX. The method of the present invention may also include measuring a number (UV) which is defined as follows:

$$UV = \sqrt{(0.5/DX)^2 + (AMo/10)^2}\ .$$

Preferably, a mixed sympathetic parasympathetic alarm long term is generated when the current value of (UV) differs from baseline by a predetermined substantial amount for approximately 30 minutes with no periods of approximately 200 heart beats where (UV) does not so differ; or a mixed sympathetic parasympathetic alarm long term is generated when the current value of (UV) differs from baseline by a predetermined substantial amount for approximately 200 heart beats during a period of approximately 2,000 heart beats.

Typically, the sharpness is characterized by a number proportional to the ratio of the Amplitude of the mode (AMo) expressed as a percentage to the difference between. substantially the largest and substantially the smallest instantaneous heart rate or RR interval in a segment (DX) to full width at half maximum of the histogram, or the sharpness is characterized by a number proportional to the ratio of the Amplitude of the mode (AMo) expressed as a percentage to the difference between substantially the largest and substantially the smallest instantaneous heart rate or RR interval in a segment (DX) to the standard. deviation of the histogram.

The present invention also provides an apparatus to perform the above-described method.

Moreover, the present invention provides an apparatus for detecting abnormal heart rate variability comprising:

A) means for first recording a subject's heart beat intervals or instantaneous heart rates over substantially no less than 50 to substantially no more than 300 heart beat intervals;

B) means for characterizing the histogram of the recorded intervals or rates comprising the number of occurrences of each of the intervals or rates recorded versus each particular interval;

C) means for indicating when a characteristic of the histogram exceeds. predetermined limits, wherein the characteristic may be any one of UV, AMo or its equivalent, DX divided by M, or AMo or its equivalent, as a function of DX or its equivalent.

The apparatus may further comprise a module strapped to the user's wrist comprising, a passive SOS Time Interval sensor, and radio means for conveying the recorded time intervals and the characteristics to a telephonic communications device. The telephonic communications device is typically a cellular telephone comprising, a strobe light, and a voice microprocessor with CPR instructions. Also, the cellular telephone has the capability of flashing the user's front door light, and the capability of unlocking the user's front door. The passive SOS sensor typically detects the Time Intervals of the pulse.

Moreover, the module may further comprise a motion sensor, means responsive to the motion sensor to distinguish between the states of coma, sleep, wakefulness, and physical activity, a galvanic skin sensor, and means responsive to the galvanic skin sensor to distinguish between the states of the connectivity, or lack of connectivity, of the wrist module to the user's wrist.

The present invention also provides:

I. A method of indicating cardiac distress comprising recording a user's baseline value of (AMo) and generating an alarm when the user's current value of (AMo) differs from the baseline value by a predetermined substantial amount for approximately 30 minutes with no periods of approximately 200 heart beats where (AMo) does not so differ. Typically, an (AMo) sympathetic alarm is generated when said current value is greater than said baseline value and/or an (AMo) parasympathetic alarm is generated when said current value is less than the baseline value.

The present invention also provides:

II. A method of indicating cardiac distress comprising recording a user's baseline value of (DX) and generating an alarm when the user's current value of (DX) differs from the baseline value by a predetermined substantial amount for approximately 30 minutes with no periods of approximately 200 heart beats where (DX) does not so differ. Typically, a (DX) sympathetic alarm is generated when the current value is less than the baseline value or a (DX) parasympathetic alarm is generated when the current value is greater than the baseline value.

The present invention also includes a method of simultaneously performing both of the above-described methods, i.e., I and II. Where both methods I and II are performed, the method may include generating a mixed sympathetic parasympathetic alarm long term when one of the alarm signals alternates with the other, and this occurs for approximately 30 minutes with no periods of approximately 200 heart beats where no alarm signal occurs. In addition to generating this alarm long term, this method may further include generating a mixed sympathetic parasympathetic alarm short term when one of the alarm signals alternates with the other and this occurs for approximately 200 heart beats during a period of 2,000 heart beats.

The present invention also provides a method for detecting abnormal heart rate variability comprising:

A) first recording a subject's heart beat intervals or instantaneous heart rates over substantially no less than 50 to substantially no more than 300 heart beat intervals;

B) characterizing the histogram of the recorded intervals or rates comprising the number of occurrences of each of the intervals or rates recorded versus each particular interval;

C) indicating when a characteristic of the histogram exceeds predetermined limits, wherein the characteristic may be any one of UV, AMo or its equivalent, DX divided by M, or AMo or its equivalent. Preferably, the characteristic is (DX) divided by M.

Typically, a sympathetic alarm is generated if the characteristic differs from baseline by a predetermined substantial amount in any two intervals within any ten contiguous intervals. Typically, the amount is approximately 0.125 times baseline or approximately 0.425 times baseline. Typically, a parasympathetic alarm signal is generated if the user's (DX) is equal to or greater than approximately 0.50 in any two intervals within any ten contiguous intervals, or a parasympathetic alarm signal is generated if the user's (AMo) is equal to or less than approximately ten in any two intervals within any ten contiguous intervals. The method may include generating a sympathetic caution-long term alarm signal if (DX) equals approximately 0.06 or less for approximately one hour or longer, and may further include generating a caution-short term alarm signal if (AMo) and (DX) vary directly with each other for approximately one hour.

BRIEF DESCRIPTION OF THE DRAWINGS

For a fuller understanding of the nature and objects of the invention reference should be had to the following detailed description taken in connection with the accompanying drawings in which:

FIG. 2 is a histogram of the numbers of equal Time Intervals between heart beats recorded from a normal user;

FIG. 3 is an overall block diagram of the apparatus according to the invention;

FIG. 8 is a detailed view of Screen A of FIG. 7;

FIG. 9 is a detailed view of Screen B of FIG. 7

FIG. 49A is a diagram showing the recorded values of the user's User Value [UV], Amplitude of the Mode [AMo], and Delta X [DX] of the shortest Mode, the next shortest Mode, and the third shortest Mode of successively recorded Time Segments of 101 Time Intervals each, which comprise a Cluster Mode according to the invention;

FIG. 49B is a diagram similar to FIG. 49A and includes the next three successively longer Modes according to the invention;

FIG. 49C is a diagram showing how [UV], [AMo], and [DX] for even shorter Modes may be inferred from the measurements indicated in FIG. 49B according to the invention;

FIG. 49D is a diagram indicating how the average [UV], average [AMo], and average [DX] are calculated for each Cluster Mode according to the invention;

FIG. 49E is a diagram showing how the OK Zone, Sympathetic ALARM Zone and Parasympathetic ALARM Zone for [UV], [AMo], and [DX] are established using various multiplier factors according to the invention;

FIG. 50 is a diagram of heart rate Time Intervals versus time for 101 Time Intervals for a normal healthy male age 63;

FIG. 51 is a diagram of heart rate Time Intervals versus time for 101 Time Intervals similar to FIG. 50 for an unhealthy male age 51;

The same reference characters refer to the same elements throughout the several views of the drawings.

BEST MODE MODE FOR CARRYING OUT THE INVENTION

Figure 1A:
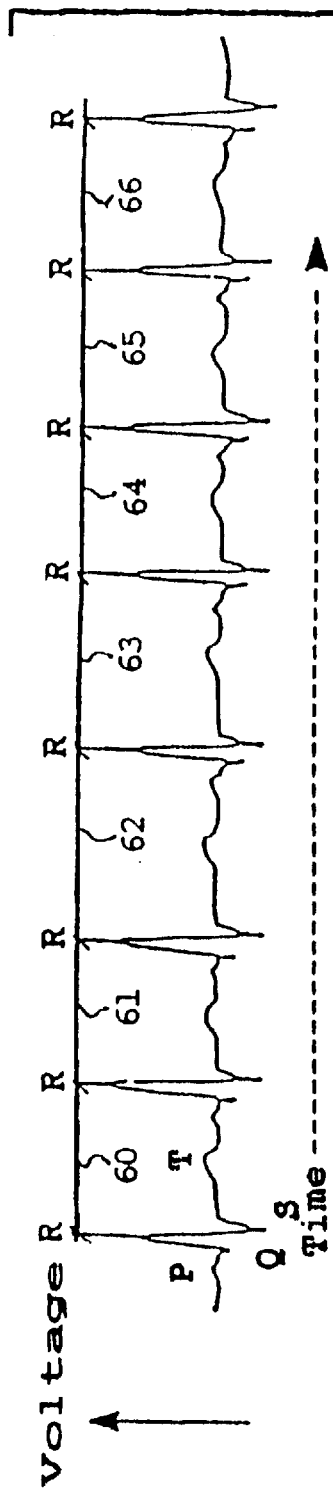
FIGS. 1A and 1B, respectively, are diagrams showing the electrocardiogram recording of a user and the user's pulse waves showing that the RR Time Intervals in the electrocardiogram are substantially equal to the corresponding Time Intervals between start of systole and start of systole.

As shown in FIG. 1A, every heart beat is composed of an electrical wave pattern called the PQRST wave. The letters indicate the important points in the wave pattern, and is generated by an electrocardiogram monitor or ECG. The letter "R" designates the peak of the PQRST wave. The Time Intervals between RR peaks are indicated at 60 to 61, 61 to 62, 62 to 63, etc.

Figure 1B:
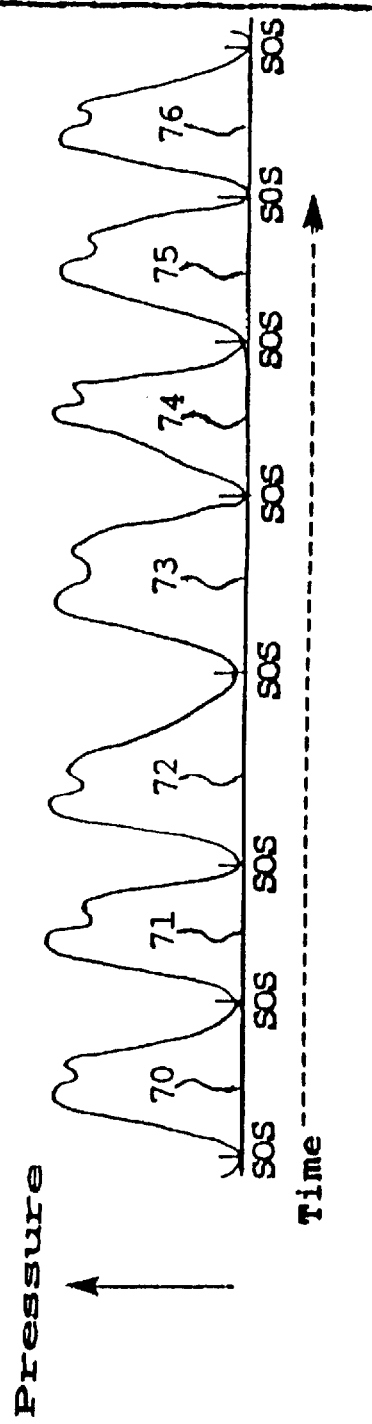

Also as shown in FIG. 1B for pulse detection, the Time Intervals between the Start of Systole to the Start of Systole, SOS. The Time Intervals between SOS troughs are indicated at 70 to 71, 71 to 72, 72 to 73, etc.

The ECG RR Time Intervals have substantially the same time duration as the pulse SOS Time Intervals and occur about a half second later than the RR Time Intervals.

FIG. 2 is a typical histogram of a 101 Time Intervals in a Time Segment. The outliers, e.g. the three longest and the three shortest Time Intervals are deleted. Delta X, [DX], is the difference between the longest Time Interval remaining and the shortest Time Interval remaining. The Mode, [Mo], is the Time Interval occurring most often in a Time Segment. The Amplitude of the Mode, [AMo], is the largest number of identical Time Intervals occurring in a Time Segment divided by the total number of Time Intervals in said Time Segment. The Median, [M], is the Time Interval in a Time Segment, in which there are equal numbers of Time Intervals equal to or larger and equal to or smaller than the Median Time Interval. As shown in FIG. 2 of a normal user, the Mode and the Mean are the same In FIG. 3, the RR Time Interval data 80 is received from an RR Time Interval sensor and the signal is processed 82, and transferred 84 to a computer 104. Also SOS Time Interval data 90 is received from an SOS Time Interval sensor and the signal processed 88, and transferred 90 to a computer 104. Also, data from a galvanic skin response sensor 92 is received and the signal processed 94, and transferred 96 to a computer 104. Also data from a motion sensor 98 is received and the signal processed 100, and transferred 102 to a computer 104. Also data from a respiratory sensor 97 and the signal processed 99, and transferred to a computer.

The results of the computer's analysis is transferred 106 to a display 108.

Figure 4B:
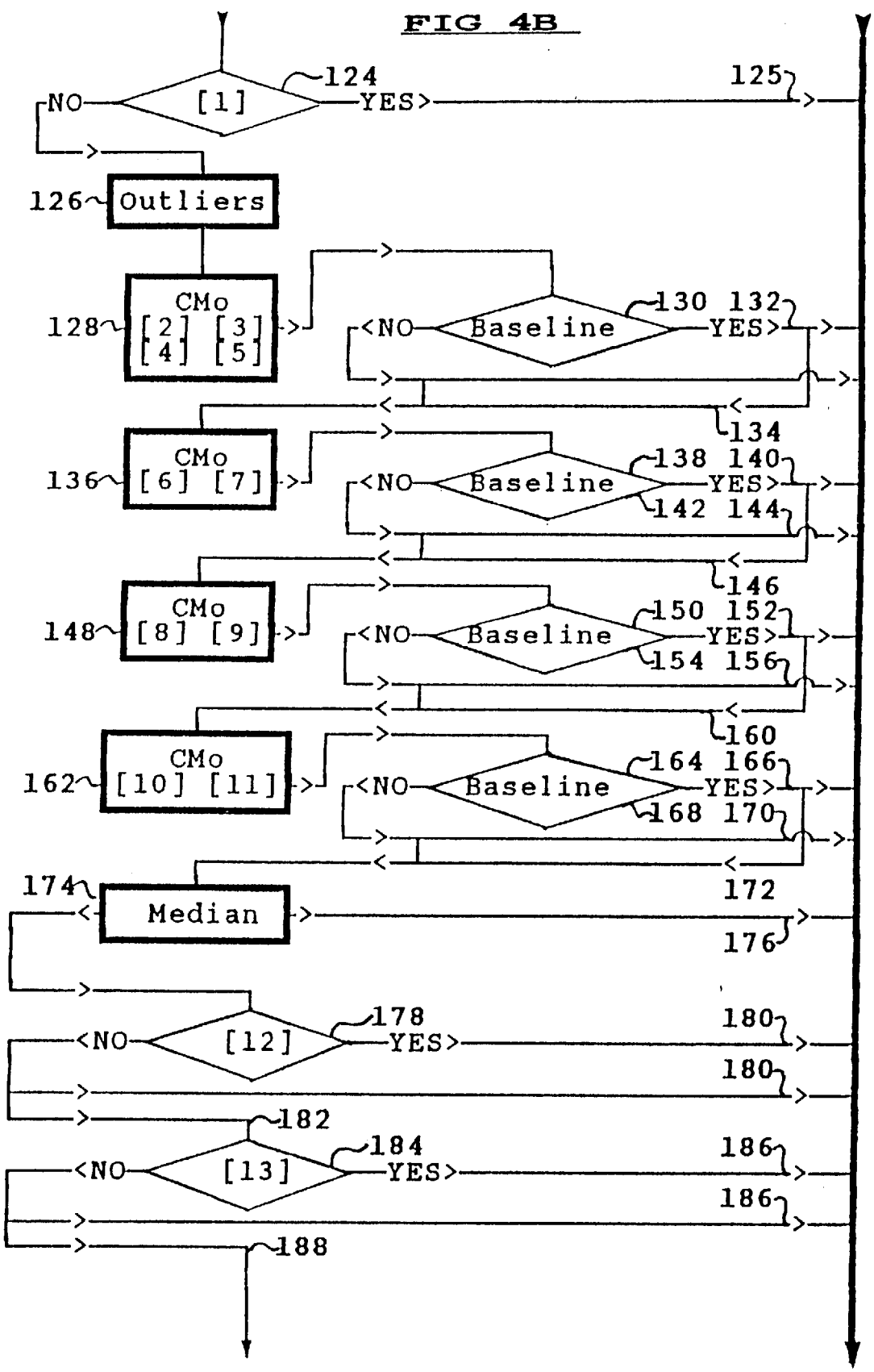
FIG. 4 is a diagram showing how FIGS. 4A, 4B, and 4C may be placed together to form FIG. 4, which is a flow chart showing the processing of a preselected number of heart beat Time Intervals to determine the seventeen ALARM and Caution conditions utilized in the invention.
Figure 4C:
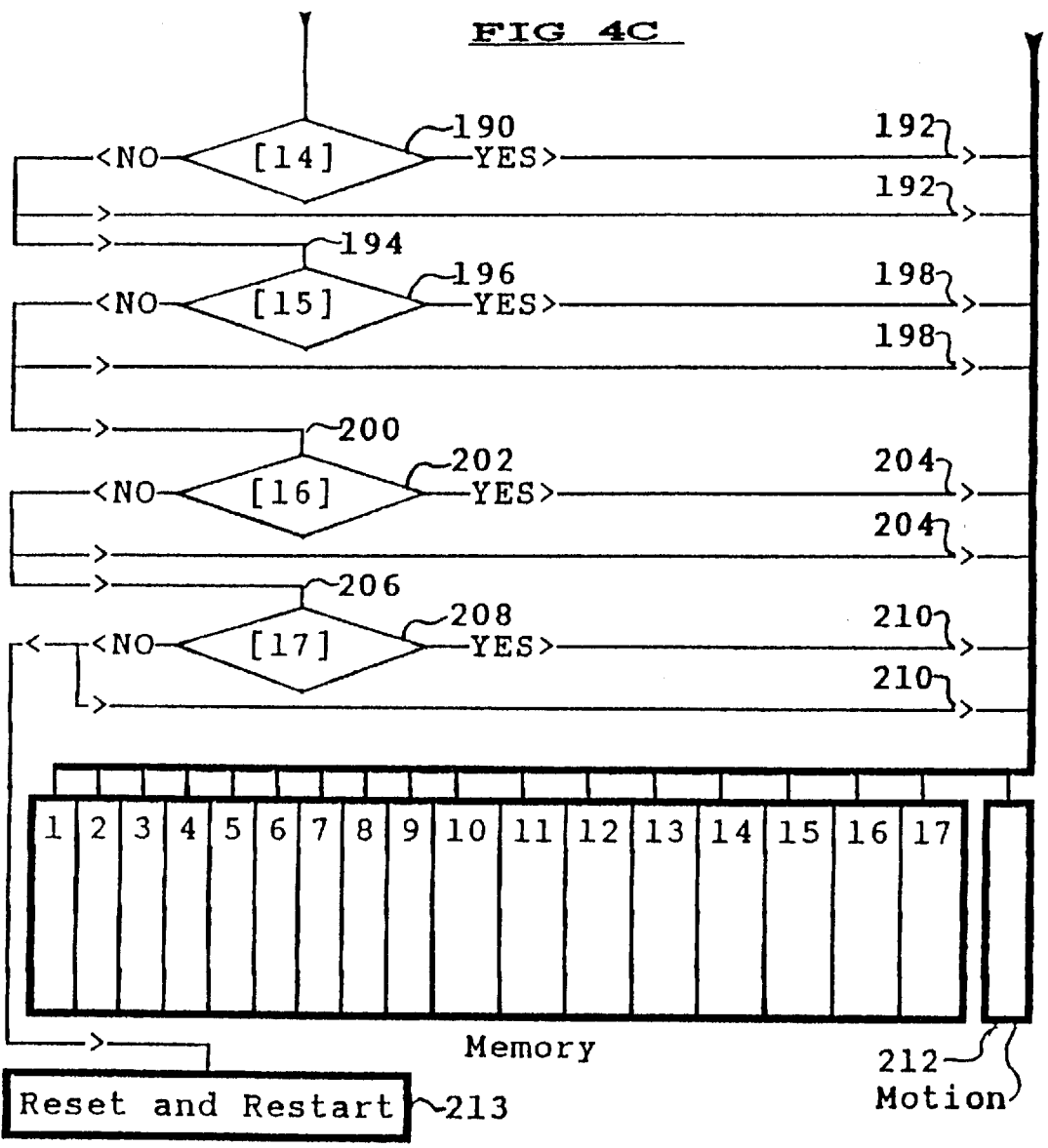

FIG. 4 is a diagram of FIGS. 4A, 4B, and 4C.

Figure 5:
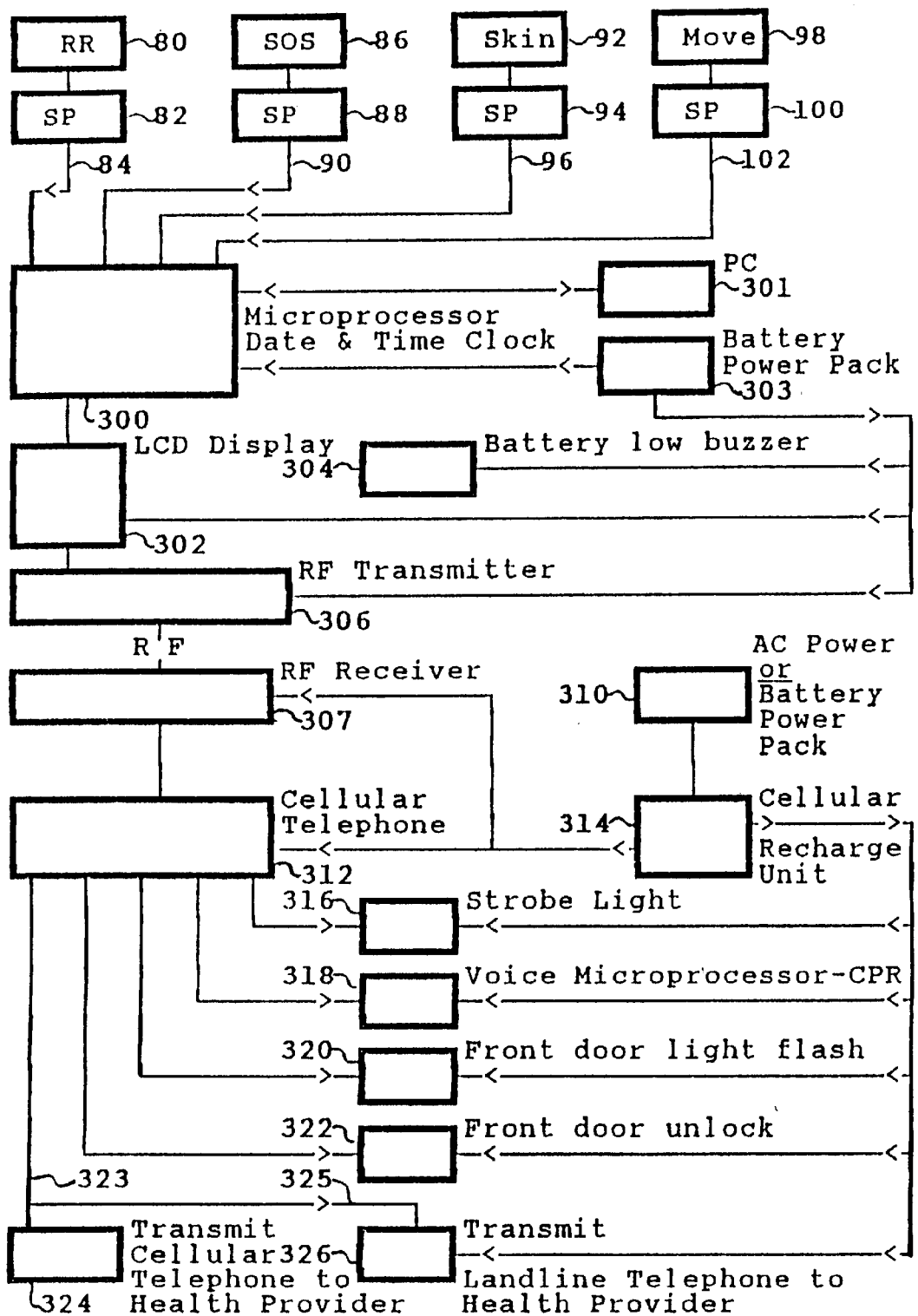
FIG. 5 is a detailed block diagram of the apparatus shown in FIG. 3.
Figure 6:
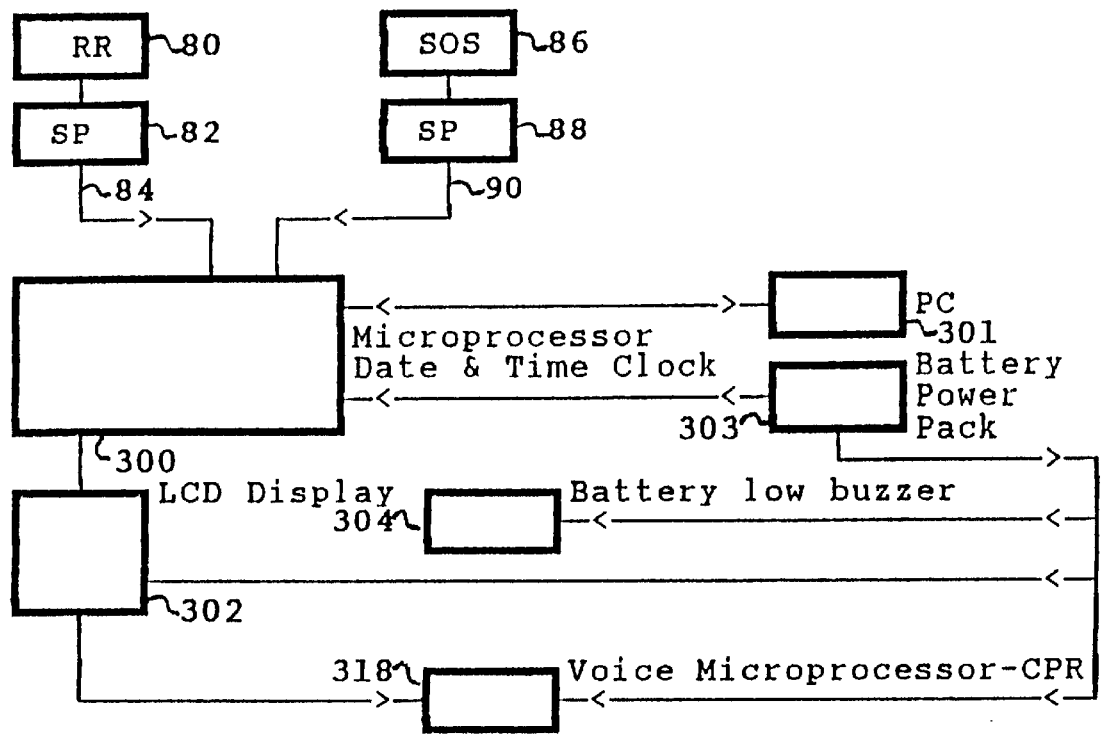
FIG. 6 is a detailed block diagram of a sports watch apparatus according to the invention.
Figure 48:
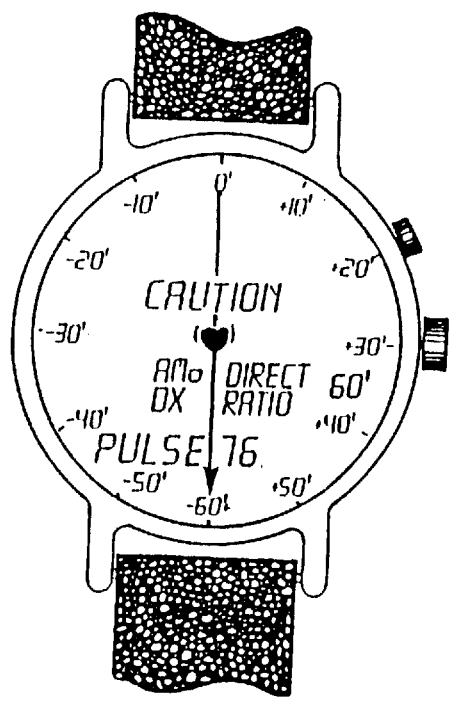

In FIG. 4A, each of the following 17 formulas is assigned a separate memory which stores four hours of ALARM, Caution and OK data in the devices diagramed in FIG. 5 and FIG. 6, and 48 hours of data in the device diagramed in FIGS. 7, 8, 9 and 10.

In FIG. 4A, RR Time Interval data 119, or SOS Time Interval data 119 is analyzed to determine if Time Interval data is being received. Also, galvanic skin response data 111 is analyzed. Motion and non-motion data 113 is analyzed and the results transferred 117 to memory 212.

If no Time Intervals are detected 110 and no motion is detected 114, and the galvanic skin response sensor data indicates the Time Interval sensor is in contact with the user 112, and this situation occurs for 10 seconds or longer, then this is a Cardiac Arrest ALARM 116.

If no Time Interval data is detected 110 and the galvanic skin response sensor 114 records no contact with the user, then the Time Interval sensor is disconnected from the user 118.

If no Time Interval data is detected 110 and the motion sensor has not recorded any movement for a predetermined period of time 114, then this a Comatose Caution 120.

Then 101 Time Intervals are accumulated in a Time Segment for further analysis 122.

Formula [1] processes a 101 Time Intervals in a Time Segment. If 20 or more PVC's are detected 124 the data is transferred 125 to memory 212. If 20 or more PVC's per Time Segment occur for a predetermined period of time then a PVC ALARM is detected. If 1 to 19 PVC's are detected, they are discarded and the next succeeding Time Intervals equal to the number discarded, replace the discarded Time Intervals until 101 Time Intervals are accumulated 119.

In FIG. 4B a Time Segment of 101 Time Intervals 122 are analyzed by the following formulas:

If no PVC's are detected, then the three longest and the three shortest Time Intervals are deleted as outliers 126.

Formulas for AMo [2][3] and DX [4][5] for each current Cluster Mode in which they occur are calculated 128 and compared with the user's recorded baseline values for AMo and DX 130. If one or more ALARMs are detected the data is transferred 132 to the appropriate memory assigned to formulas [2][3][4] and [5] 212. If one or more ALARMs occurs for a predetermined period of time, interrupted by single, non-contiguous OR Time Segments, if any, then one or more of four ALARMs are detected, e.g. An Amo Sympathetic ALARM [2], an AMo Parasympathetic ALARM [3], a DX Sympathetic ALARM [4], a DX Parasympathetic ALARM [5], as the case may be 130. If an ALARM is detected and if no ALARM is detected 134, the 101 Time Intervals in the Time Segment 122 are analyzed by the next formula [6] 136.

If a combination of Sympathetic ALARMs. [2] and [4], and Parasympathetic ALARMs, [3] and [5] occur for a predetermined period of time, interrupted by single, non-contiguous OK Time Segments,if any, then a Mixed Sympathetic/Parasympathetic ALARM-Long Term [6] is detected 138. If an ALARM is detected by formula [6], the data is transferred 140 to the memory assigned to formula [6] 212. If an ALARM is detected and if no ALARM is detected 146, the data is transferred 144 to the appropriate memory assigned to formula [6], and the 101 Time Intervals in the Time Segment 122 are analyzed by the next formula [7] 148.

If a combination of Sympathetic ALARMs, [2] and [4], and Parasympathetic ALARMs. [3] and [5] occur in a single Time Segment, in a predetermined percentage of 10 continuous Time Segments, then a Mixed Sympathetic/Parasympathetic ALARM-Short Term [7] is detected 142. If an ALARM is detected by formula [7], the data is transferred 144 to the memory assigned to formula [7] 212. If an ALARM is detected and if no ALARM is detected 146 the data is transferred 144 to the appropriate memory assigned to formula [7], and the 101 Time Intervals in the Time Segment 122 are analyzed by the next formula [8] 148.

The formula for UV Sympathetic [8] for each current Cluster Mode in which it occurs is calculated and compared with the user's recorded baseline values for UV 150. If an ALARM occurs for a predetermined period of time, interrupted by single, noncontiguous OK Time Segments, if any, then an ALARM is detected, e.g. a UV Sympathetic Alarm [8] 148. If an ALARM is detected by formula [8], the data is transferred 152 to the memory assigned to formula [8] 212. If an ALARM is detected and if no ALARM is detected 160, the data is transferred 152 to the appropriate memory assigned to formula [8], and the 101 Time Intervals in the Time Segment 122 are analyzed by the next formula [9] 148.

The formula for UV ParasymPathetic [9] for each current Cluster Mode in which it occurs is calculated and compared with the user's recorded baseline values for UV 154. If an ALARM occurs for a predetermined period of time, interrupted by single, non-contiguous OK Time Segments, if any, then an ALARM is detected, e.g. a UV Parasympathetic Alarm [9] 148. If an ALARM is detected by formula [9], the data is transferred 156 to the memory assigned to formula [9] 212. If an ALARM is detected and if no ALARM is detected 160, the data is transferred 156 to the appropriate memory assigned to formula [9], and the 101 Time Intervals in the Time Segment 122 are analyzed by the next formula [10] 162.

If a combination of UV Sympathetic ALARMs [8] and UV Parasympathetic ALARMs [9] occur for a predetermined period of time, interrupted by single, non-contiguous OK Time Segments, if any, then a Mixed UV Sympathetic/ParasymPathetic ALARM-Long Term [10] is detected 162.

If an ALARM is detected by formula [10], the data is transferred 166 to the memory assigned to formula [10] 212. If an ALARM is detected and if no ALARM is detected 172, the data is transferred 166 to the appropriate memory assigned to formula [7], and the 101 Time Intervals in the Time Segment 122 are analyzed by the next formula [11] 162.

If a combination of UV Sympathetic ALARMs [8] and UV Parasympathetic ALARMs [9], occur in a single Time Segment, in a predetermined percentage of 10 continuous Time Segments, then a Mixed UV Sympathetic/Parasympathetic ALARM-Short Term [11] is detected 162. If an ALARM is detected by formula [11], the data is transferred 170 to the memory assigned to formula [11] 212. If an ALARM is detected and if no ALARM is detected 172, the data is transferred 170 to the appropriate memory assigned to formula [7], and the 101 Time Intervals in the Time Segment 122 are analyzed and the Median, [M], is calculated 174.

The Median, [M], Time Interval of the current Time Segment is calculated 174 and the Time Intervals in the Time Segment 122 are analyzed by the next formula [12] 178.

If within a Time Segment, DX divided by the Median, [M], 174 equals or is less than 0.125 the data is transferred 180 to the memory assigned to formula [12] 212. If within a Time Segment, DX divided by the Median equals or is less than 0.125 occurs in a predetermined percentage of 10 continuous Time Segments, then a Sympathetic Type II ALARM [12] 178 is detected. Also, if within a Time Segment, DX divided by the Median equals or is more than 0.125 but less than 0.425 182, and the data is transferred 180 to the memory assigned to formula [12] 212, and the Time Intervals in the Time Segment 122 are analyzed by the next formula [13] 184.

If within a Time Segment, DX divided by the Median, [M] 174 equals or is more than 0.425 the data is transferred 186 to the memory assigned to formula [13] 212. If within a Time Segment, DX divided by the Median equals or is more than 0.425 occurs in a predetermined percentage of 10 continuous Time Segments, then a Parasympathetic Type II ALARM [13] 184 is detected. Also, if within a Time Segment, DX divided by the Median equals or is more than 0.125 but less than 0.425 184 the data is transferred 186 to the memory assigned to formula [13] 212, and the Time Intervals in the Time Segment 122 are analyzed by the next formula [14] 190.

If within a single Time Segment, DX equals or is more than 0.50 190 the data is transferred 192 to the memory assigned to formula [14] 212. If this occurs in a predetermined percentage of 10 continuous Time Segments, then a Parasympathetic ALARM Type III [14] 190 is detected. Also, if within a Time Segment, DX is less than 0.50, the data is transferred 192 to the memory assigned to formula [14] 212, and the Time Intervals in the Time Segment 122 are analyzed by the next formula [15] 196.

If within a single Time Segment, AMo equals or is less than 10 196, the data is transferred 198 to the memory assigned to formula [15] 212. If this occurs in a predetermined percentage of 10 continuous Time Segments, then a Parasympathetic Type IV ALARM [15] 196 is detected. Also, if within a Time Segment, AMo is more than 10 200, the data is transferred 198 to the memory assigned to formula [15] 212, and the Time Intervals in the Time Segment 122 are analyzed by the next formula [16] 202.

FIG. 4C is the continued analysis of a Time Segment of 101 Time Intervals 122 made by the following formulas:

If DX is equal or less than 0.06 202, the data is transferred 204 to the memory assigned to formula [16] 212. If this occurs for a percentage of a predetermined period of the time, then a Sympathetic Caution-Long Term [16] 202 is detected. Also, if DX is more than 0.06 206, the data is transferred 204 to the memory assigned to formula [16] 212, and the Time Intervals in the Time Segment 122 are analyzed by the next formula [17] 208.

If AMo and DX vary directly with each other 208, the data is transferred 210 to the memory assigned to formula [17] 212. If this occurs for a percentage of a predetermined period of time, then a Caution-Short Term [17] 208 is detected. Also, if AMo and DX do not vary directly, the data is transferred 210 to the memory assigned to formula [17] 212, and the count of new Time Intervals in the next succeeding Time Segment commences 213.

In FIG. 5, A microprocessor with a date and time clock 300 gathers Time Interval data from a Time Interval sensor 80 or 86, and from a motion sensor 98 and a galvanic skin response sensor 92. ALARM, Caution and OK stress data is stored in the microprocessor memory and dated and time stamped by the date and time clock 300. The stress data accumulated for the user can be down loaded to a PC 301. Also the multiplier factors and time durations for the 17 formulas can be programmed and reprogrammed by the user's health care provider 324.

The user's stress status is displayed on a liquid crystal diode 302. If the battery has less than a 20% charge a buzzer notifies the user 304.

The battery power pack 303 supplies electricity to operate the components 80 through 306.

The user's stress status is transmitted by a low power RF transmitter 306 to a receiver 308 inside the cellular telephone 312.

If the cellular telephone 312 is recharging in the cellular telephone recharge unit 314 and an ALARM is received, then the strobe light 316 is activated on the cellular telephone 312, and the voice microprocessor broadcasts 318 from the cellular telephone earpiece speaker CPR instructions, and the user's front door light starts to flash 320, and the front door is unlocked by activating an electric door strike 322, and an ALARM message is transmitted by the cellular telephone 312, first by attempting a landline connection 323 to a health care provider 324, and failing a landline connection 325, then on cellular frequencies to 313 to a health care provider 324.

In FIG. 6, A microprocessor with a date and time clock 300 gathers Time Interval data, 80 or 86, from a Time Interval sensor 80 or 86. ALARM, Caution and OK stress data is stored in the microprocessor memory and dated and time stamped by the date and time clock 300. The stress data accumulated for the user can be down loaded to a PC 301. Also the multiplier factors and time durations for the 17 formulas can be programmed and re-programmed by the user's health care provider 324.

The battery power pack 303 supplies electricity to operate the components 80 through 318.

The user's stress status is displayed on a liquid crystal diode 302, and the voice microprocessor broadcasts from a micro speaker CPR instructions 318. If the battery has less than a 20% charge a buzzer notifies the user 304.

Figure 7:
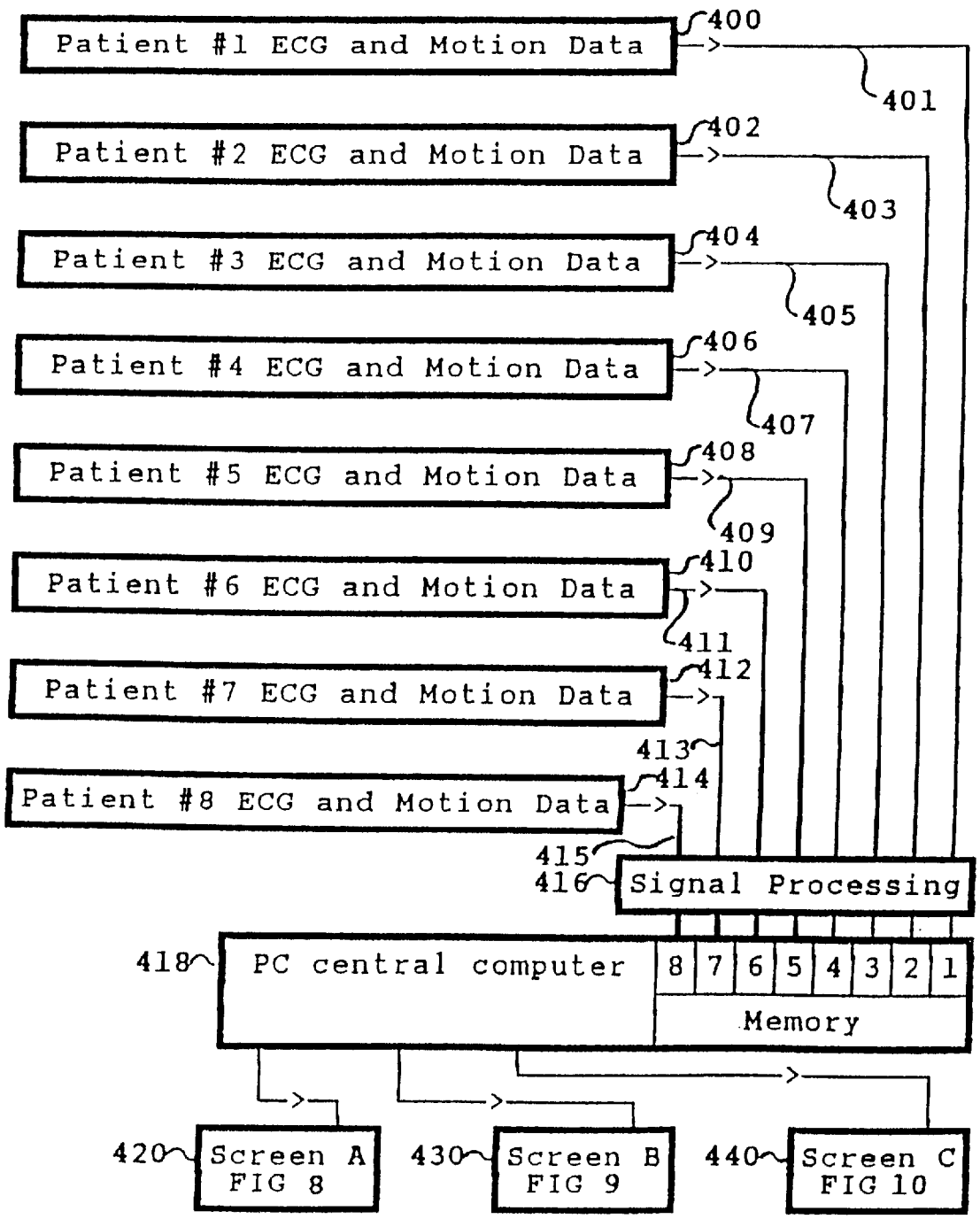
FIG. 7 is a block diagram of a multiple patient monitoring apparatus according to the invention.

FIG. 7 illustrates a single channel ECG apparatus for eight patient users 400 through 414 in hospital critical care units. The RR Time Interval data for each patient user and each-signal processed 416 and downloaded to a central PC 418, which analyzes each user's stress status and displays this information on a monitor, FIG. 8, Screen A, 420 FIG. 9, Screen B, 430 and FIG. 10, Screen C, 440.

FIG. 8, Screen A is the eight patient monitor which displays the user patient's name, room and bed number, and the current values for each user patient's UV, AMo, and DX, the PVC count, and heart rate in Beats Per Minute. In addition, Screen A displays each user patient's UV, AMo, and DX ALARM status, the setting in minutes of when an ALARM would be triggered and the number of minutes an ALARM condition, if any, has persisted. In the FIG. 8 example, user patient 8, in the current Time Segment has experienced a UV of 40.1, an AMo of 80, a DX of 0.06, 7 PVC's, which indicate a Sympathetic UV, AMo, and DX ALARM, and that this ALARM Condition has persisted for 31 minutes, or one minute longer than the 30 minute ALARM set point.

If a user patient experiences an ALARM, the health care provider on duty can display an individual user's recent stress record, as illustrated in FIG. 9, Screen B.

In the left hand column are the user patient's name, room and bed designation. Below this information. Below this information are the ALARM Settings comprised of the baseline formulas for UV, AMo, and DX, the multiplier factors used to establish the user patient's Sympathetic and Parasympathetic ALARM Zones, and the values derived, which trigger an ALARM condition. Below this are the ALARM durations, which cause an ALARM to be triggered.

In the central column are displayed the user patient's values for UV, AMo, DX, and PVC's together the user patient's heart rate in BPM and the ALARM set.

In the right hand column are the time duration of each of the ALARM conditions displayed in the central column.

Figure 10:
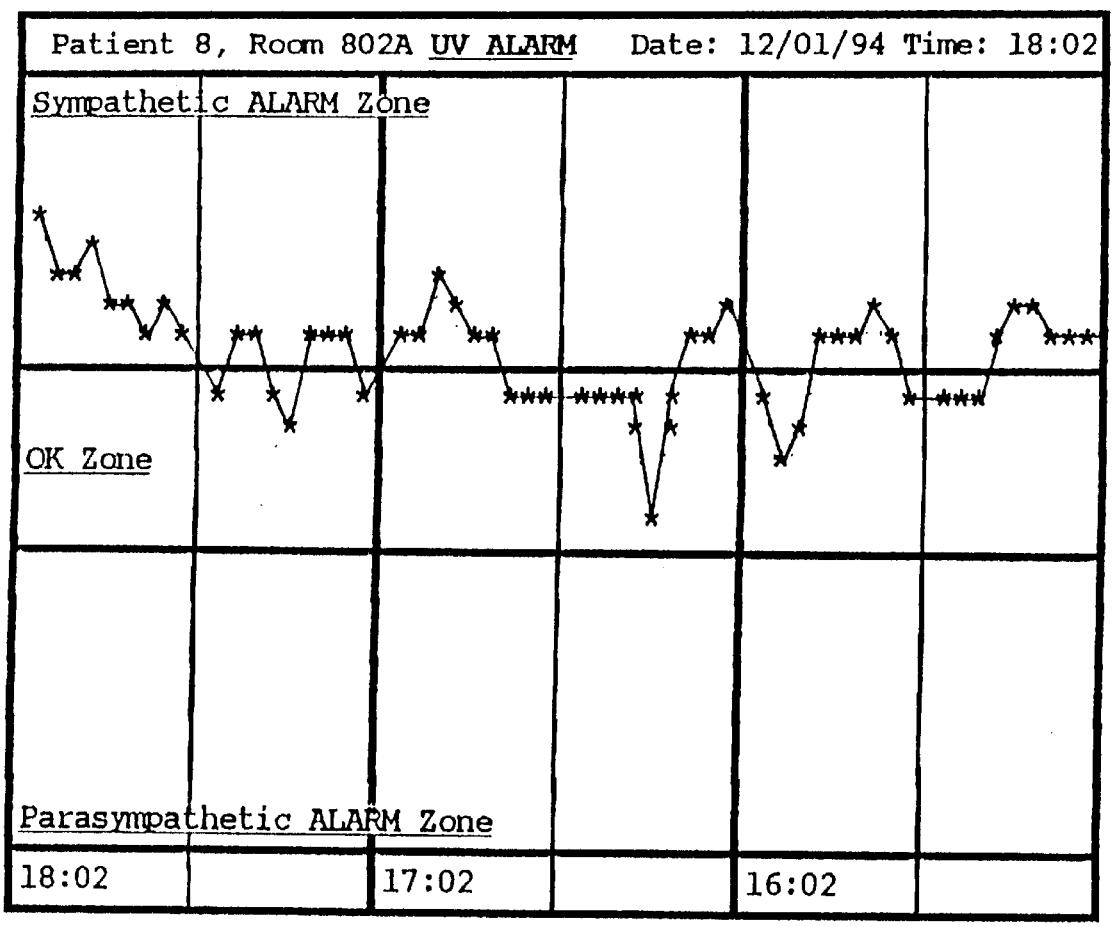
FIG. 10 is a detailed view of Screen C of FIG. 7.

The health care provider can view a graphic illustration of a user's recent stress record illustrated in FIG. 10, Screen C.

Figure 11:
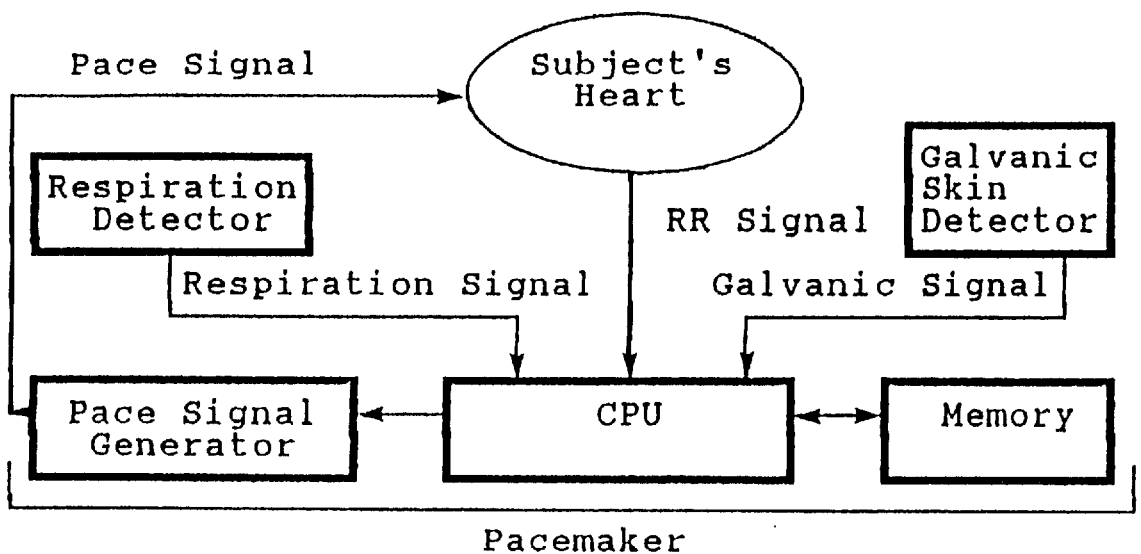
FIG. 11 is a block diagram of a pacemaker, which also may be part of a cardioverter defibrillator with a pacemaker according to the invention.

As shown in FIG. 11, if the CPU in a cardioverter defibrillator with a pacemaker or a pacemaker detects an ALARM condition in the User's Heart, as described in FIG. 4A, 4B, and 4C, then, based on the additional data from the Respiration Detector and the Galvanic Skin Detector, the Pace Signal Generator will commence pacing the User's Heart for a predetermined period of time.

Figure 12:
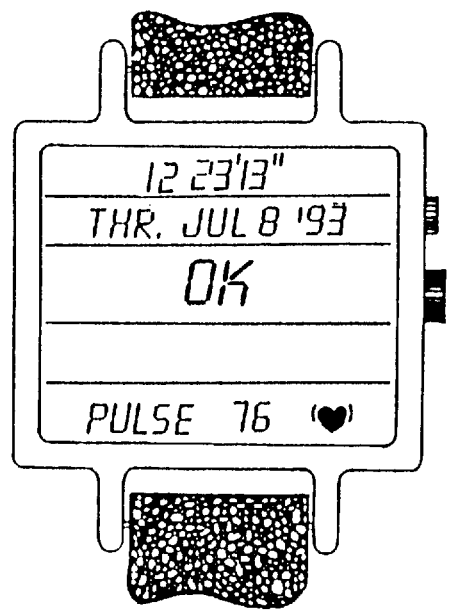
FIGS. 12 through 48 show various displays for FIG. 5 and FIG. 6 according to the invention.

FIG. 12 illustrates a rectilinear digital display format of the wrist unit component described in FIG. 5 and FIG. 6. The top line displays the date, the second line the time, the third line the user's stress or distress status, the fourth line the type of distress based on one or more of the 17 distress formulas discussed elsewhere, and the fifth line the user's pulse and the symbol for a heart indicating the galvanic skin response sensor is gathering pulse data from the user. In the FIG. 12 example, the user's stress/distress state is OK.

Figure 13:
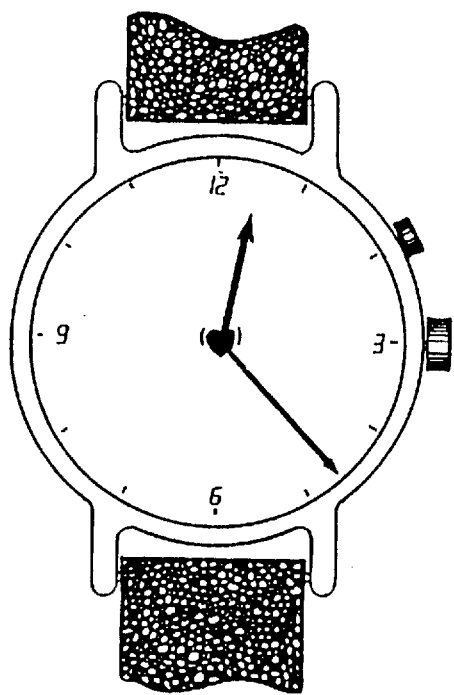

FIG. 13 illustrates an alternative round analog/digital standard watch format screen of the wrist unit component described in FIG. 5 and FIG. 6.

Figure 14:
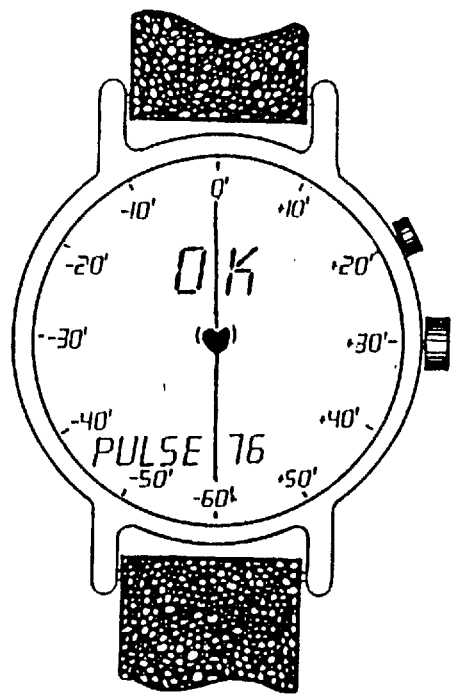

FIG. 14 illustrates the stress/distress screen on the round analog/digital standard watch format of the wrist unit component described in FIG. 5 and FIG. 6. The left hemisphere of the screen is for the display of the type of distress based on one or more of the seventeen, [1]–[17], distress formulas discussed elsewhere. The numbers from 0 at the 12 o'clock position going counterclockwise to −60 at the 6 o'clock position indicate the duration of a parasympathetic alarm in minutes. The numbers from 0 at the 12 o'clock position going clockwise to +60 at the 6 o'clock position indicate the duration of a sympathetic alarm in minutes. At the center of the two hemispheres is the symbol for a heart indicating the galvanic skin response sensor is gathering pulse data. The user's pulse is displayed at the bottom of the screen. In FIG. 14 the user's stress/distress state is OK.

Figure 15:
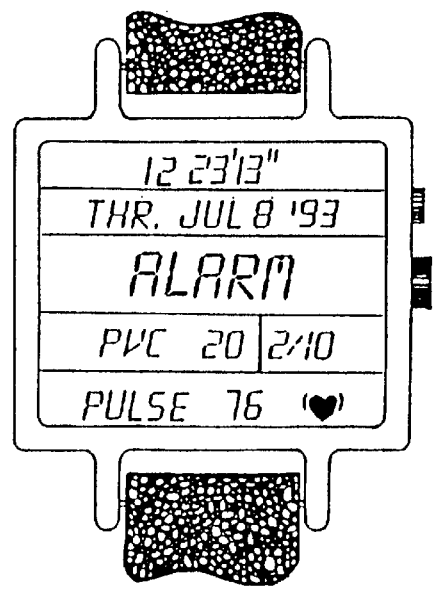

FIG. 15 illustrates a user's ALARM in the digital format based on the first, [1], stress formula, discussed elsewhere, and is based on 20 or more premature ventricular contractions, PVC's per Time Segment. This information is displayed on the fourth line of the digital format screen along with the type of activity, which in this example is 20 PVC's per Time Segment, and the duration of the over activity, which in this example is two out of the ten previous Time Segments.

Figure 16:
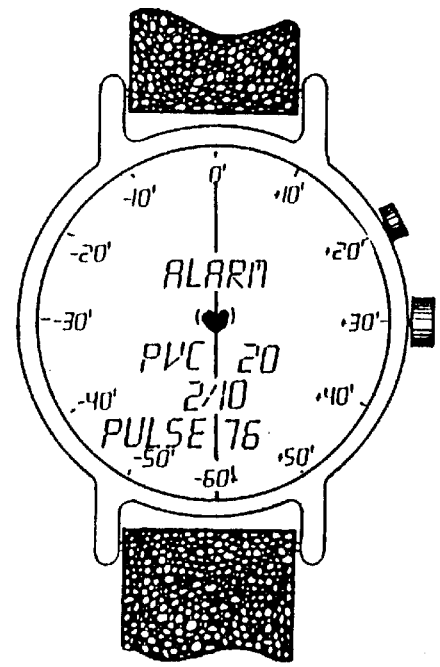

FIG. 16 illustrates a user's ALARM on the stress/distress screen of the round analog/digital standard watch based format on the first, [1], stress formula, discussed elsewhere, and is based on 20 or more PVC's per Time Segment. This information is displayed in the center of the two hemispheres of the analog/digital format screen. The type of over activity, which in this example is 20 PVC's, and the duration of the over activity, which in this example is two out of the previous ten Time Segments.

Figure 17:
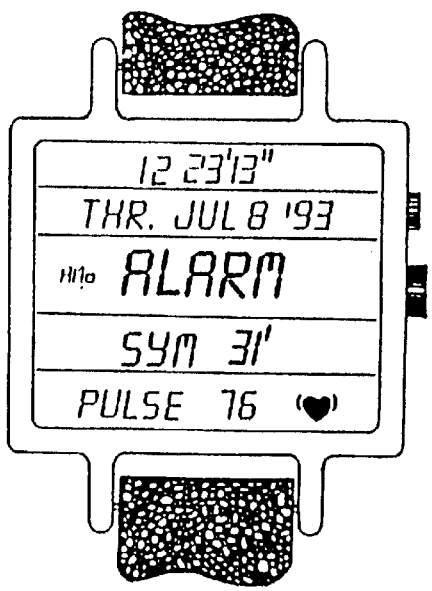

FIG. 17 illustrates a user's ALARM in the digital format based on the second, [2] stress formula, discussed elsewhere, and is based on an over active sympathetic AMo. This information is displayed on the fourth line of the digital format screen along with the type of over activity, which in this example is sympathetic, and the duration of the over activity, which in this example is 31 minutes.

Figure 18:
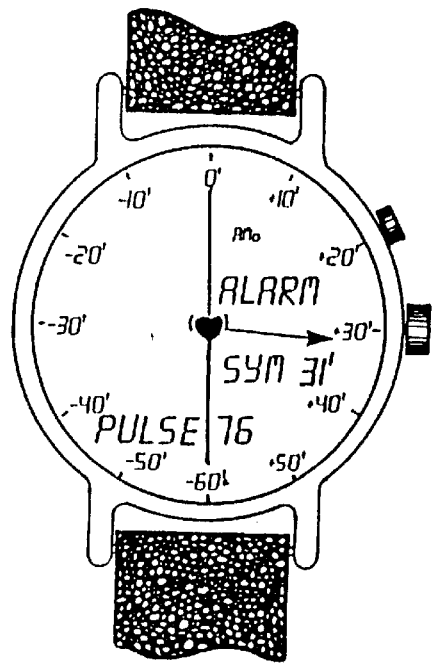

FIG. 18 illustrates a user's ALARM on the stress/distress screen of the round analog/digital standard watch based format on the second, [2] stress formula, discussed elsewhere, and is based on an over active sympathetic AMo. This information is displayed in the right hemisphere of the analog/digital format screen. The type of over activity, which in this example is sympathetic, and the duration of the over activity, which in this example is 31 minutes.

Figure 19:
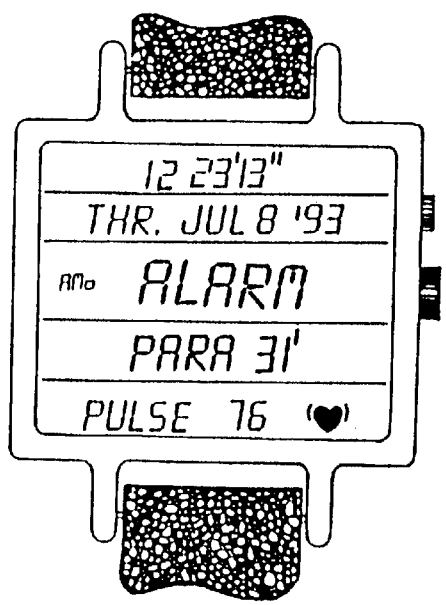

FIG. 19 illustrates a user's ALARM in the digital format based on the third, [3] stress formula, discussed elsewhere, and is based on an over active parasympathetic AMo. This information is displayed on the fourth line of the digital format screen along with the type of over activity, which in this example is parasympathetic, and the duration of the over activity, which in this example is 31 minutes.

Figure 20:
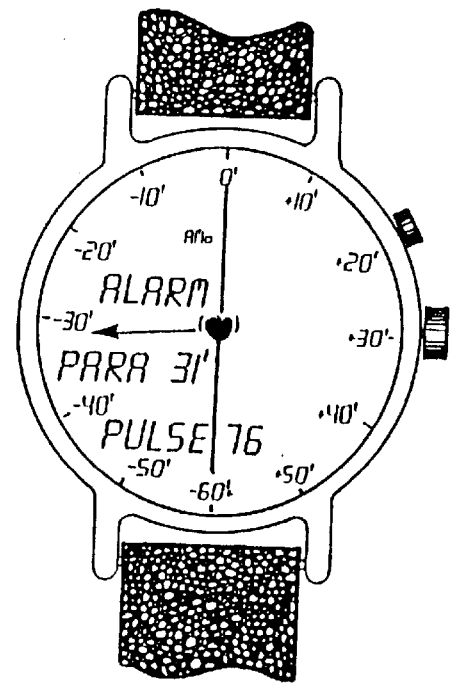

FIG. 20 illustrates a user's ALARM on the stress/distress screen of the round analog/digital standard watch based format on the third, [3] stress formula, discussed elsewhere, and is based on an over active parasympathetic AMo. This information is displayed in the left hemisphere of the analog/digital format screen. The type of over activity, which in this example is parasympathetic, and the duration of the over activity, which in this example is 31 minutes.

Figure 21:
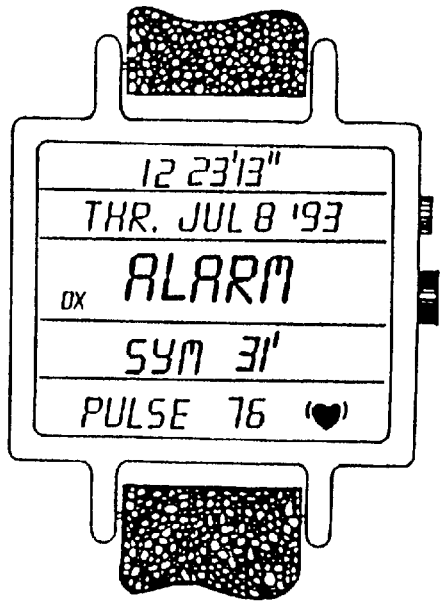

FIG. 21 illustrates a user's ALARM in the digital format based on the fourth, [4] stress formula, discussed elsewhere, and is based on an over active sympathetic DX. This information is displayed on the fourth line of the digital format screen along with the type of over activity, which in this example is sympathetic, and the duration of the over activity, which in this example is 31 minutes.

Figure 22:
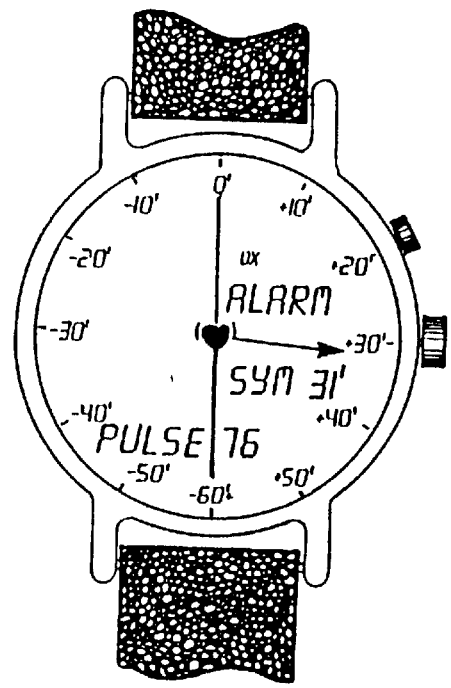

FIG. 22 illustrates a user's ALARM on the stress/distress screen of the round analog/digital standard watch based format on the fourth, [4] stress formula, discussed elsewhere, and is based on an over active sympathetic DX. This information is displayed in the right hemisphere of the analog/digital format screen. The type of over activity, which in this example is sympathetic, and the duration of the over activity, which in this example is 31 minutes.

Figure 23:
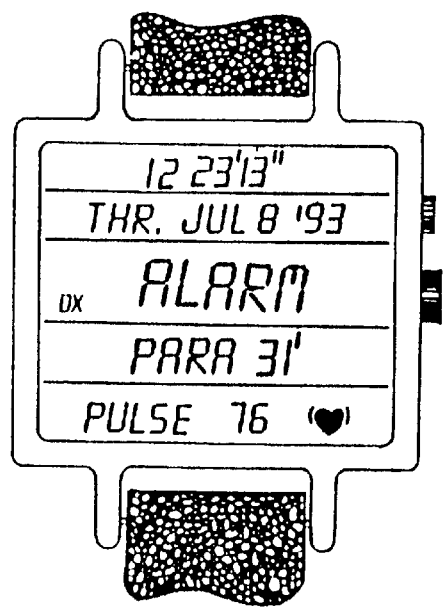

FIG. 23 illustrates a user's ALARM in the digital format based on the fourth, [4] stress formula, discussed elsewhere, and is based on an over active parasympathetic DX. This information is displayed on the fourth line of the digital format screen along with the type of over activity, which in this example is parasympathetic, and the duration of the over activity, which in this example is 31 minutes.

Figure 24:
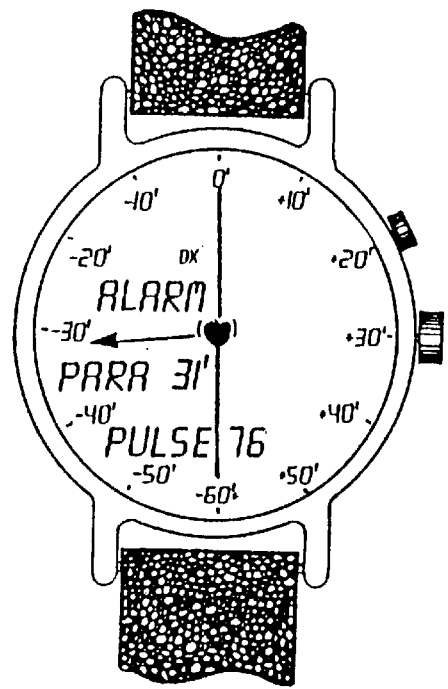

FIG. 24 illustrates a user's ALARM on the stress/distress screen of the round analog/digital standard watch based format on the fourth, [4] stress formula, discussed elsewhere, and is based on an over active parasympathetic DX. This information is displayed in the left hemisphere of the analog/digital format screen. The type of over activity, which in this example is parasympathetic, and the duration of the over activity, which in this example is 31 minutes.

Figure 25:
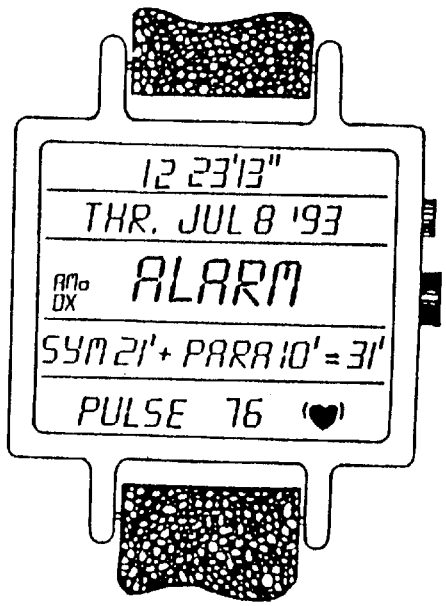

FIG. 25 illustrates a user's ALARM in the digital format based on the sixth, [6], stress formula, discussed elsewhere, and is based on an over active sympathetic and parasympathetic AMo and DX. This information is displayed on the fourth line of the digital format screen along with the type of over activity, which in this example is both sympathetic and parasympathetic, and the duration of the over activity, which in this example is 21 minutes of sympathetic and 10 minutes of parasympathetic over activity.

Figure 26:
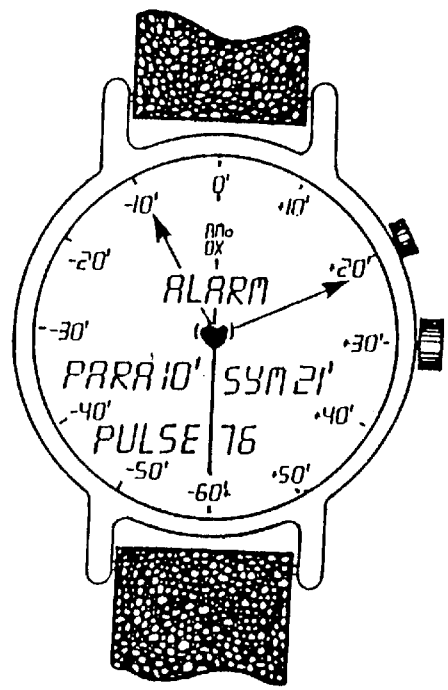

FIG. 26 illustrates a user's ALARM on the stress/distress screen of the round analog/digital standard watch based format on the sixth, [6], stress formula, discussed elsewhere, and is based on an over active sympathetic and parasympathetic AMo and DX. This information is displayed in the center of the two hemispheres of the analog/digital format screen. The type of over activity, which in this example is both sympathetic and parasympathetic, and, the duration of the over activity, which in this example is 21 minutes of sympathetic and 10 minutes of parasympathetic over activity.

Figure 27:
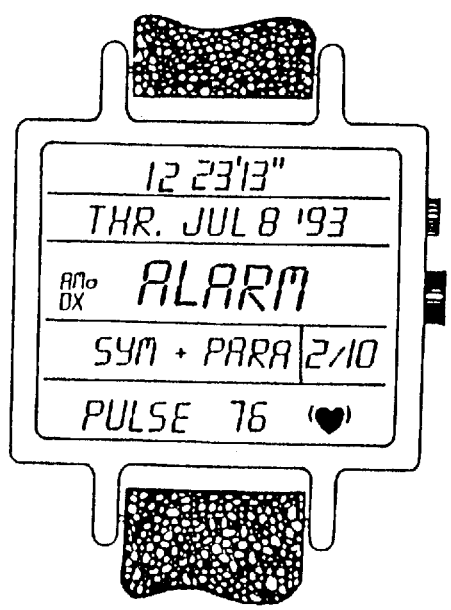

FIG. 27 illustrates a user's ALARM in the digital format based on the seventh, [7], stress formula, discussed elsewhere, and is based on an over active sympathetic and parasympathetic AMo and DX within a single Time Segment. This information is displayed on the fourth line of the digital format screen along with the type of over activity, which in this example is both sympathetic and parasympathetic, and the duration of the over activity, which in this example is two out of the previous ten Time Segments.

Figure 28:
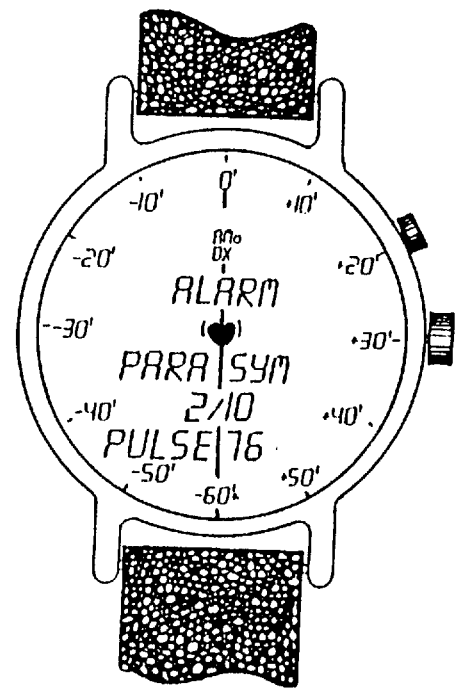

FIG. 28 illustrates a user's ALARM of the stress/distress screen on the round analog/digital standard watch based format on the seventh, [7], stress formula, discussed elsewhere, and is based on an over active sympathetic and parasympathetic AMo and DX within a single Time Segment. This information is displayed in the center of the two hemispheres of the analog/digital format screen. The type of over activity, which in this example is both sympathetic and parasympathetic, and the duration of the over activity, which in this example is two out of the previous ten Time Segments.

Figure 29:
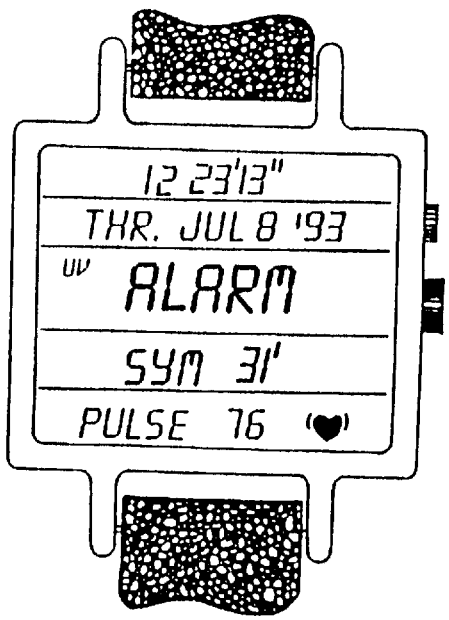

FIG. 29 illustrates a user's ALARM in the digital format based on the eighth, [8] stress formula, discussed elsewhere, and is based on an over active sympathetic UV. This information is displayed on the fourth line of the digital format screen along with the type of over activity, which in this example is sympathetic, and the duration of the over activity, which in this example is 31 minutes.

Figure 30:
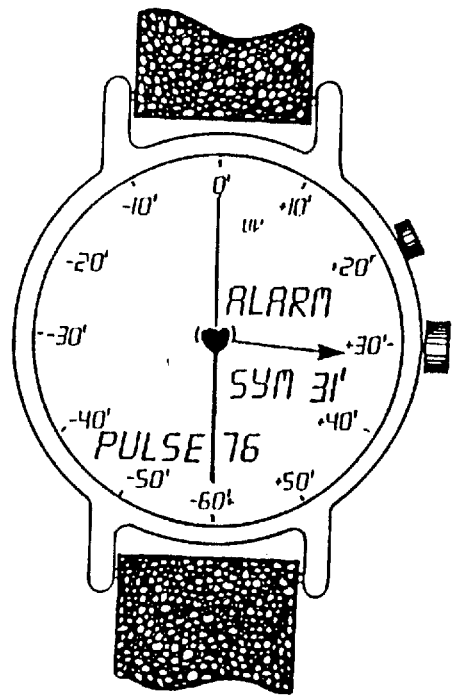

FIG. 30 illustrates a user's ALARM on the stress/distress screen of the round analog/digital standard watch based format on the eighth, [8] stress formula, discussed elsewhere, and is based on an over active sympathetic UV. This information is displayed in the right hemisphere of the analog/digital format screen. The type of over activity, which in this example is sympathetic, and the duration of the over activity, which in this example is 31 minutes.

Figure 31:
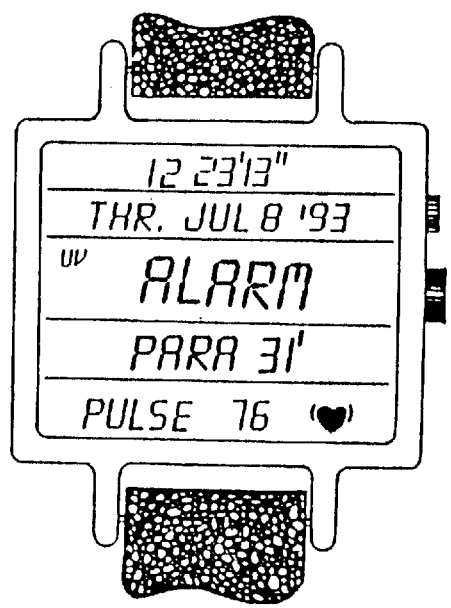

FIG. 31 illustrates a user's ALARM in the digital format based on the ninth, [9] stress formula, discussed elsewhere, and is based on an over active parasympathetic UV. This information is displayed on the fourth line of the digital format screen along with the type of over activity, which in this example is parasympathetic, and the duration of the over activity, which in this example is 31 minutes.

Figure 32:
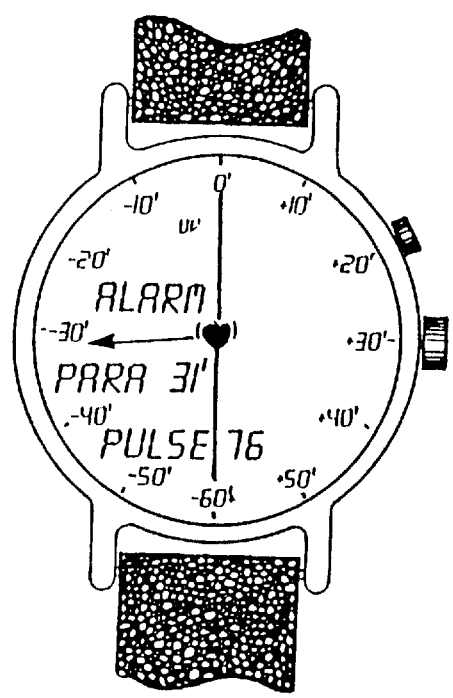

FIG. 32 illustrates a user's ALARM on the stress/distress screen of the round analog/digital standard watch based format on the ninth, [9] stress formula, discussed elsewhere, and is based on an over active parasympathetic UV. This information is displayed in the left hemisphere of the analog/digital format screen. The type of over activity, which in this example is parasympathetic, and the duration of the over activity, which in this example is 31 minutes.

Figure 33:
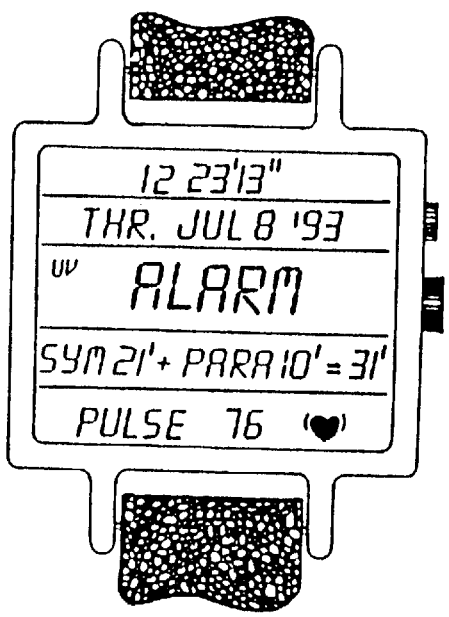

FIG. 33 illustrates a user's ALARM in the digital format based on the tenth, [10], stress formula, discussed elsewhere, and is based on an over active sympathetic and parasympathetic UV. This information is displayed on the fourth line of the digital format screen along with the type of over activity, which in this example is both sympathetic and parasympathetic, and the duration of the over activity, which in this example is 21 minutes of sympathetic and 10 minutes of parasympathetic over activity.

Figure 34:
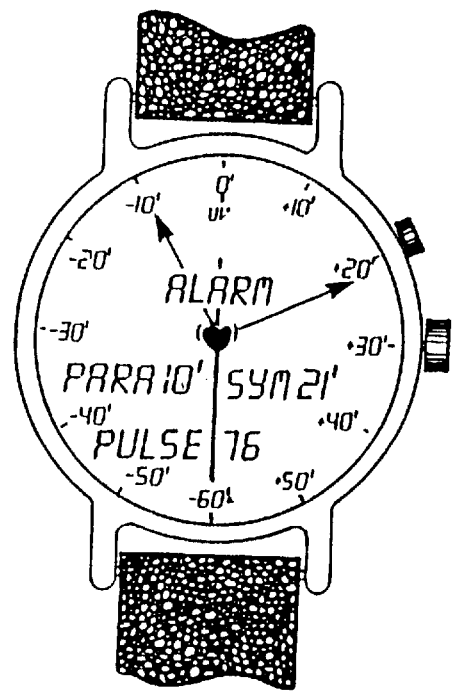

FIG. 34 illustrates a user's ALARM on the stress/distress screen of the round analog/digital standard watch based format on the tenth, [10], stress formula, discussed elsewhere, and is based on an over active sympathetic and parasympathetic UV. This information is displayed in the center of the two hemispheres of the analog/digital format screen. The type of over activity, which in this example is both sympathetic and parasympathetic, and the duration of the over activity, which in this example is 21 minutes of sympathetic and 10 minutes of parasympathetic over activity.

Figure 35:

FIG. 35 illustrates a user's ALARM in the digital format based on the eleventh, [11], stress formula, discussed elsewhere, and is based on an over active sympathetic and parasympathetic UV within a single Time Segment. This information is displayed on the fourth line of the digital format screen along with the type of over activity, which in this example is both sympathetic and parasympathetic, and the duration of the over activity, which in this example is two out of the previous ten Time Segments.

Figure 36:

FIG. 36 illustrates a user's ALARM of the stress/distress screen on the round analog/digital standard watch based format on the eleventh, [11], stress formula, discussed elsewhere, and is based on an over active sympathetic and parasympathetic UV within a single Time Segment. This information is displayed in the center of the two hemispheres of the analog/digital format screen. The type of over activity, which in this example is both sympathetic and parasympathetic, and the duration of the over activity, which in this example is two out of the previous ten Time Segments.

Figure 37:
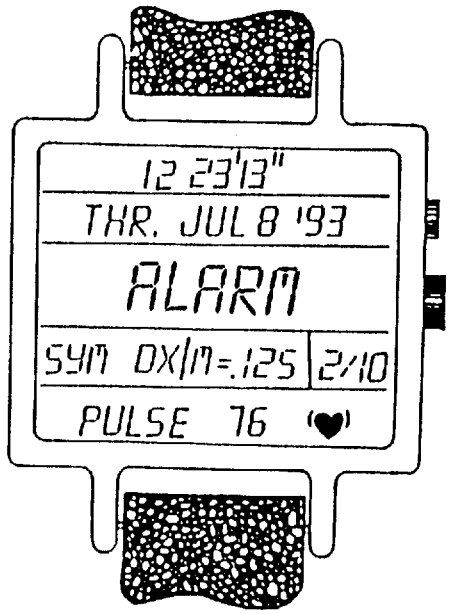

FIG. 37 illustrates a user's ALARM in the digital format based on the twelfth [12] stress formula, discussed elsewhere, and is based on an over active sympathetic system. This information is displayed on the fourth line of the digital format screen along with the type of over activity, which in this example is sympathetic, and the duration of the over activity, which in this example is two out of the previous ten Time Segments.

Figure 38:
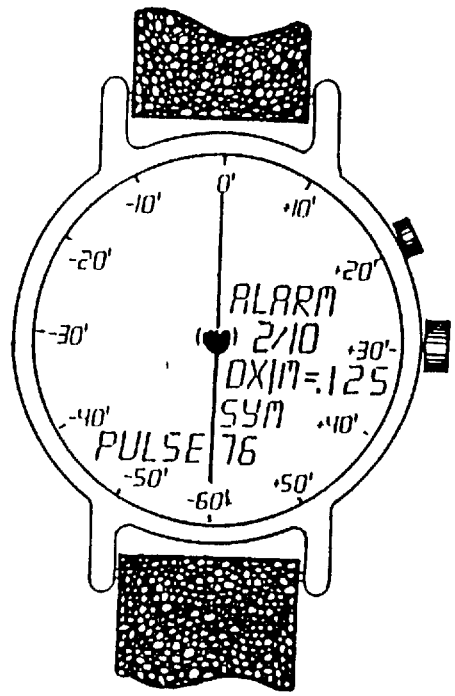

FIG. 38 illustrates a user's ALARM on the stress/distress screen of the round analog/digital standard watch based format on the twelfth, [12], stress formula, discussed elsewhere, and is based on an over active sympathetic system. This information is displayed in the right hemisphere of the analog/digital format screen. The type of over activity, which in this example is sympathetic, and the duration of the over activity, which in this example is two out of the previous ten Time Segments.

Figure 39:

FIG. 39 illustrates a user's ALARM in the digital format based on the thirteenth [13] stress formula, discussed elsewhere, and is based on an over active parasympathetic system. This information is displayed on the fourth line of the digital format screen along with the type of over activity, which in this example is parasympathetic, and the duration of the over activity, which in this example is two out of the previous ten Time Segments.

Figure 40:
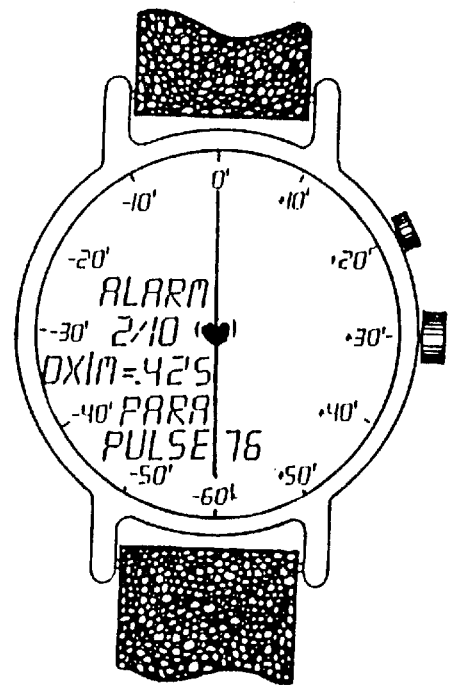

FIG. 40 illustrates a user's ALARM on the stress/distress screen of the round analog/digital standard watch based format on the thirteenth, [13], stress formula, discussed elsewhere, and is based on an over active parasympathetic system. This information is displayed in the left hemisphere of the analog/digital format screen. The type of over activity, which in this example is parasympathetic, and the duration of the over activity, which in this example is two out of the previous ten Time Segments.

Figure 41:
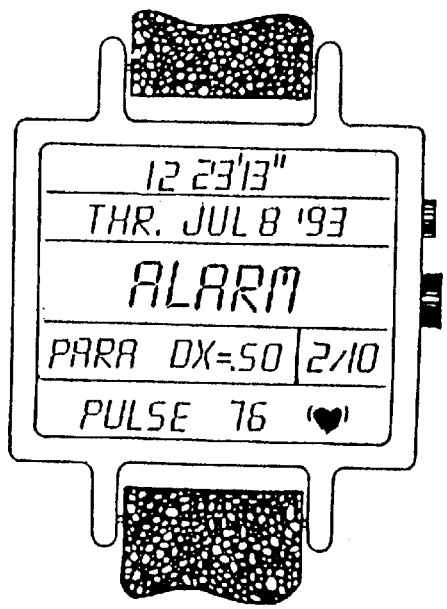

FIG. 41 illustrates a user's ALARM in the digital format based on the fourteenth, [14], stress formula, discussed elsewhere, and is based on an over active parasympathetic system. This information is displayed on the fourth line of the digital format screen, along with the type of over activity, which in this example is parasympathetic, and the duration of the over activity, which in this example is two out of the previous ten Time Segments.

Figure 42:
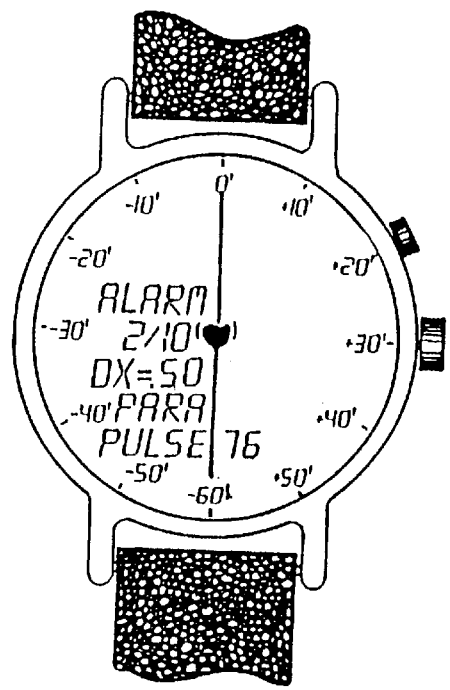

FIG. 42 illustrates a user's ALARM on the stress/distress screen of the round analog/digital standard watch based format on the fourteenth, [14], stress formula, discussed elsewhere, and is based on an over active parasympathetic system. This information is displayed in the left hemisphere of the analog/digital format screen. The type of over activity, which in this example is parasympathetic, and the duration of the over activity, which in this example is two out of the previous ten Time Segments.

Figure 43:
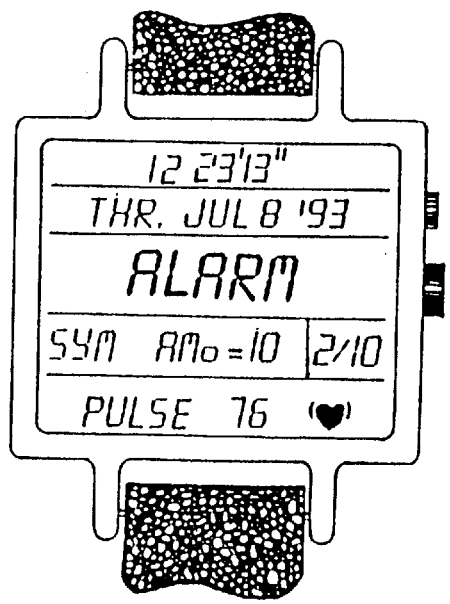

FIG 43 illustrates a user's ALARM in the digital format based on the fifteenth, [15], stress formula, discussed elsewhere, and is based on an over active sympathetic system. This information is displayed on the fourth line of the digital format screen along with the type of over activity, which in this example is sympathetic, and the duration of the over activity, which in this example is two out of the previous ten Time Segments.

Figure 44:
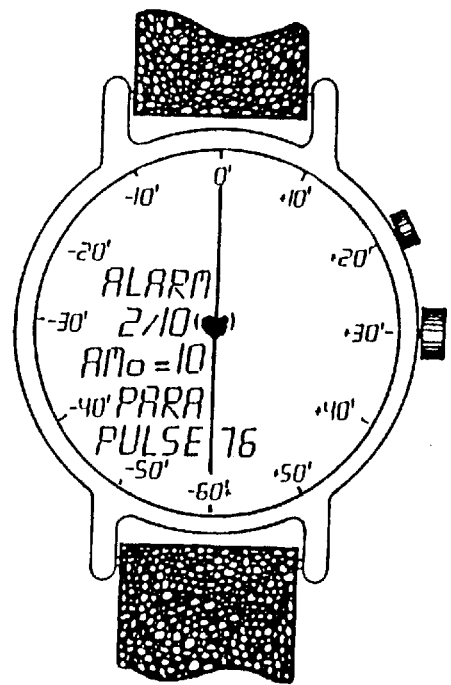

FIG. 44 illustrates a user's ALARM on the stress/distress screen of the round analog/digital standard watch based format on the fifteenth, [15], stress formula, discussed elsewhere, and is based on an over active sympathetic system. This information is displayed in the left hemisphere of the analog/digital format screen. The type of over activity, which in this example is sympathetic, and the duration of the over activity, which in this example is two out of the previous ten Time Segments.

Figure 45:
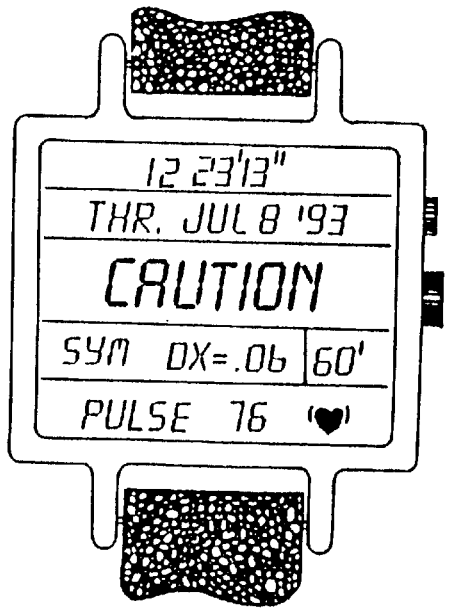

FIG. 45 illustrates a user's Caution in the digital format based on the sixteenth [16] stress formula, discussed elsewhere, and is based on an over active sympathetic system. This information is displayed on the fourth line of the digital format screen along with the type of over activity, which in this example is sympathetic, and the duration of the over activity, which in this example is 60 minutes.

Figure 46:
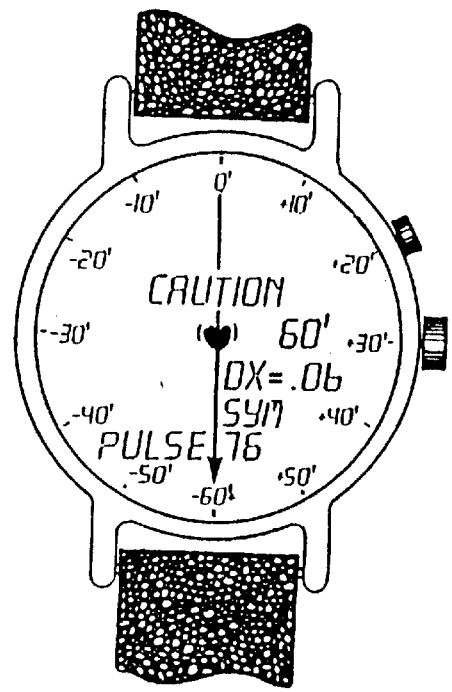

FIG. 46 illustrates a user's Caution on the stress/distress screen of the round analog/digital standard watch based format on the sixteenth, [16], stress formula, discussed elsewhere, and is based on an over active sympathetic system. This information is displayed in the right hemisphere of the analog/digital format screen. The type of over activity, which in this example is sympathetic, and the duration of the over activity, which in this example is 60 minutes.

Figure 47:
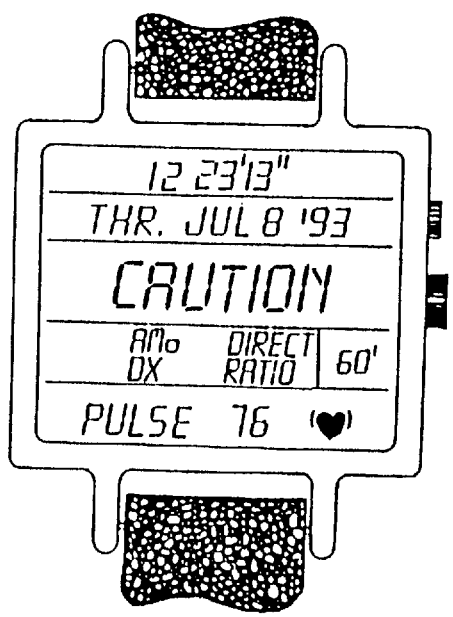

FIG. 47 illustrates a user's Caution in the digital format based on the seventeenth, [17], stress formula, discussed elsewhere, and is based on the direct ratio of AMo and DX to each other. This information is displayed on the fourth line of the digital format screen along with the type of activity, which in this example is the direct ratio of AMo and DX to each other, and the duration of the over activity, which in this example is 60 minutes.

FIG. 48 illustrates a user's Caution on the stress/distress screen of the round analog/digital standard watch based format on the seventeenth, [17], stress formula, discussed elsewhere, and is based on the direct ratio of AMo and DX to each other. This information is displayed in the center of the two hemispheres of the analog/digital format screen. The type of activity, which in this example is the direct ratio of AMo and DX to each other, and the duration of the activity, which in this example is 60 minutes.

If more than one Caution or ALARM is detected, then each such state is displayed in the appropriate location on the watch face starting with the condition generated by the first, [1], formula and ending with the seventeenth, [17], formula. Each such Caution or ALARM is displayed for five seconds.

Figure 49:
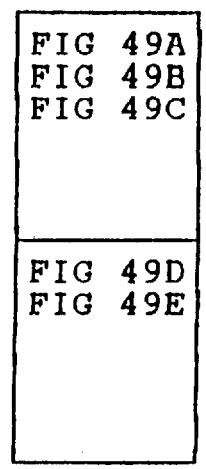
FIG. 49 is a diagram showing how FIGS. 49A, 49B, 49C, 49D and 49E may be placed together to form FIG. 49, which is a flow chart showing the processing of a preselected number of heart beat Time Intervals to determine the user's OK Zone, the Sympathetic ALARM Zone, the Parasympathetic ALARM Zone, and the multiplier factors, which determine an ALARM according to the invention.

FIG. 49A represents the minimum number, (3), of daytime Modes needed to create a user's recorded Cluster Mode, which begins with the shortest recorded Mode, (Mo 1), and progresses to the next shortest, (Mo 2) and the next shortest (Mo 3). These Modes are 0.02 seconds longer than the previous Mode. The respective recorded user values for UV, AMo, and DX for each Mode are shown. An attempt should be made to record two hours of the user's nighttime Modes. This should produce a matrix that looks like FIG. 49B.

FIG. 49B illustrates two user recorded Cluster Modes and the user values for UV, AMo, and DX. For data to be valid in the 2nd Cluster Mode, it must contain three or more entries. If this approach fails, then there is a need to infer the values for UV, AMo, and DX using ratio and proportion. Thus, [UV2:UV3::UV3::UV4], and [UV3:UV4::UV4:UV5], etc., etc. Also values should be inferred for UV, AMo, and DX for shorter Modes so that there is a minimum of three Cluster Modes as shown in FIG. 49C.

In FIG. 49C The three values for UV, Amo, and DX in each Cluster Mode are averaged, which establishes the user's baseline UV, AMo, and DX in each Cluster Mode.

In FIG. 49D the ALARM multiplier factors are inserted to establish the sympathetic and parasympathetic ALARM Zones, and thus the OK Zone between the two ALARM Zones.

If the Mode of a 101 Time Interval Time Segment falls within the 1st Cluster Mode of X to X+0.04, then the ALARM levels designated for this Cluster Mode are used. If a Mode is sensed that is not within one of the three minimum Cluster Modes, then the ALARM levels in the Cluster Mode whose values are closest to user's current values are used.

In FIG. 50, the patient's heart rhythm is variable. This is evidenced by DX=0.16 and AMo=27, which is characteristic of a natural autonomic balance between the sympathetic and the parasympathetic nervous system.

In FIG. 51, the patient's heart rhythm is not variable. This is evidenced by DX=0.04 and AMo=52, which is characteristic of an over active sympathetic nervous system.

Figure 52:
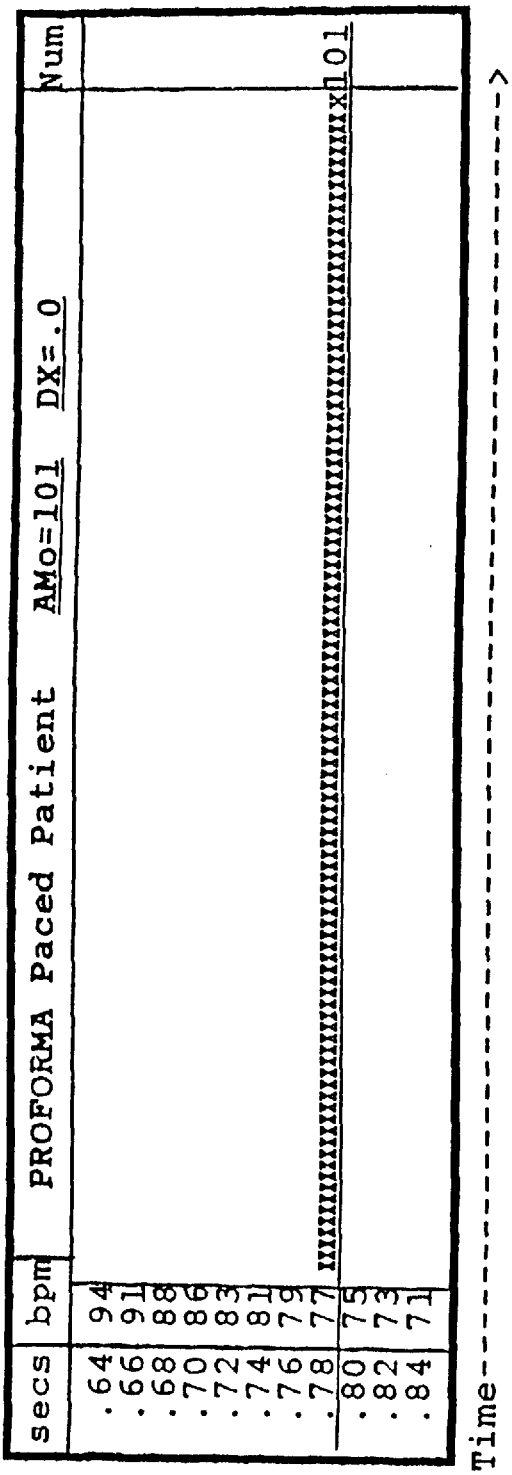
FIG. 52 is a diagram of heart rate Time Intervals versus time for 101 Time Intervals similar to FIG. 50 which shows how patients are presently paced with a pacemaker using a constant heart rate Time Interval.

In FIG. 52 the patient's heart paced by a pacemaker or a cardioverter defibrillator with a pacemaker has no heart rhythm variability. This is evidenced by DX=0 and AMo=101, which is characteristic of an extremely over active sympathetic nervous system.

Figure 53:
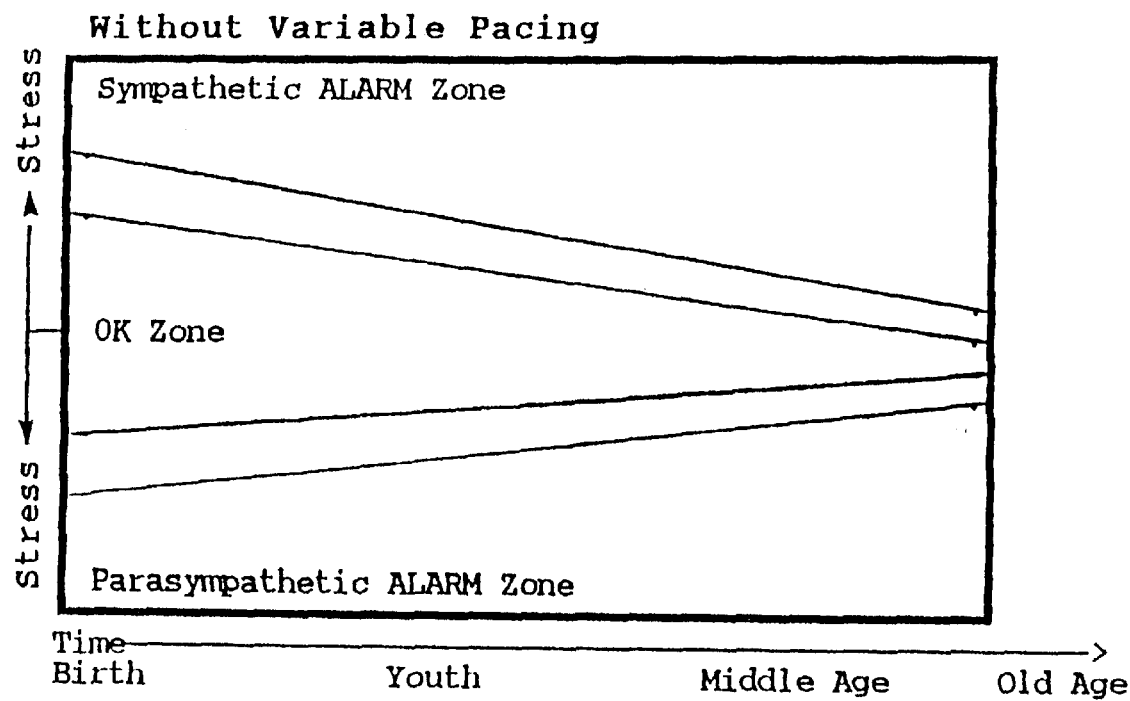
FIG. 53 is a diagram which shows how heart rate variability decreases thus narrowing the OK Zone over a human's life time.

FIG. 53 At birth and through youth, the heart's OK Zone regarding variability is wide. With the onset of middle age and into old age the heart's OK Zone regarding variability narrows. A deviation in the heart's variability of more than approximately +15% indicates an over stressed sympathetic system in the Sympathetic ALARM Zone, and a deviation of more than −15% indicates an over stress parasympathetic system in the Parasympathetic ALARM Zone.

Figure 54:
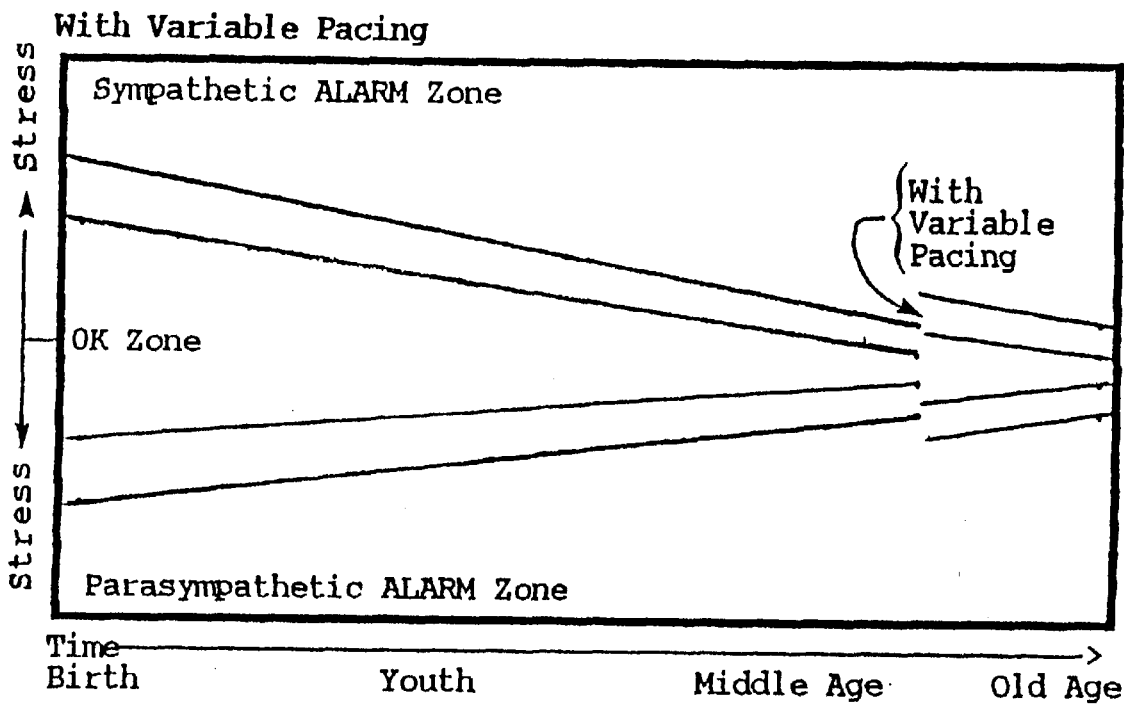
FIG. 54 is a diagram, similar to FIG. 53, which shows how, with variable pacing, the user's OK Zone may be expanded to be similar to that of a younger subject according to the invention.

FIG. 54 The inventors suggest a user patient's life can be prolonged by first detecting the onset of an arrythmia before it occurs and then, (1) pacing the patient with his/her own naturally variable heart rhythm or (2) pacing the patient using the variable heart rhythm of a healthy individual matched to the patient's age, sex and physical condition, or (3) using a random number generator programmed to emulate the heart rhythm of a healthy individual matched to the patient's age, sex and physical condition.

Just as pacing a patient with bradycardia treats the symptom and prolongs life, so the inventors suggest that pacing a user patient with a narrow heart rhythm variability with a wider heart rhythm variability treats the symptom and will prolong the user patient's life.

Figure 55:
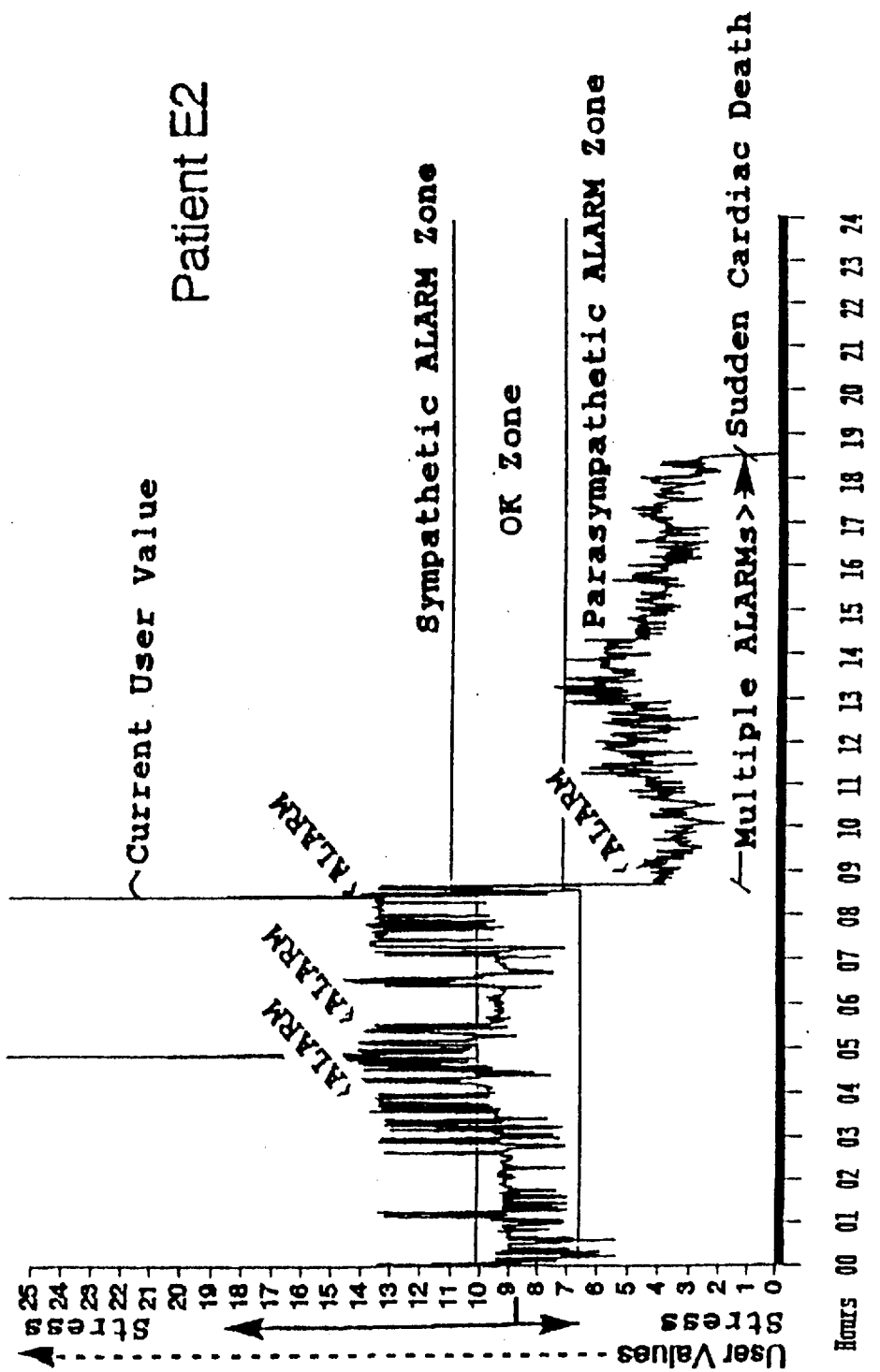
FIG. 55 is a record of User Values [UV] of a cardiac patient which shows how the [UV] ALARMS indicating an over active sympathetic nervous system were activated three times prior to sudden cardiac death, and how a change from an over active sympathetic nervous system to an over active parasympathetic nervous system occurred approximately 10 hours prior to sudden cardiac death triggering multiple [UV] ALARMS until sudden cardiac death.

FIG. 55 is a chart of Patient E2's ECG Holter monitor tape as interpreted by FIG. 4A, 4B, and 4C using formulas [8] and [9], e.g. User Value.

From hour 00 to hour 02 Patient E2's baseline is established for two Cluster Modes. Using a multiplier factor, E2's OK Zone is established between the Sympathetic ALARM Zone at 10.1, and the Parasympathetic ALARM Zone at 6.6. Thus, E2's UV OK Zone is between 10.1 and 6.6.

Starting in Hour 03 through Hour 08, Patient E2 experienced three episodes of approximately 30 miniutes each of an over active Sympathetic system, which triggered three UV Sympathetic ALARMs [8]. Halfway through Hour 08, Patient E2's autonomic nervous system suddenly changed from an over active Sympathetic response to an over active Parasympathetic response triggering a fourth ALARM, a Mixed UV Sympathetic/Parasympathetic ALARM-Short Term [11]. From halfway through Hour 08 to halfway through Hour 18, when Patient E2 expired due to Sudden Cardiac Death, Patient E2's autonomic nervous system experienced an almost continuous over active parasympathetic response triggering multiple UV Parasympathetic ALARMs [9].

Halfway though Hour 08, Patient E2's OK zone between UV 10.1 and 6.6 changed to between UV 10.9 and 7.0, because E2's heart rate changed from approximately 77 beats per minute to approximately 71 beats per minute, thus changing the Cluster Mode, which determined the Uv Sympathetic and Parasympathetic ALARM Zones.

PACEMAKER

AND

CARDIOVERTER DEFIBRILLATOR WITH A PACEMAKER

As previously mentioned, if the CPU in a cardioverter defibrillator with a pacemaker or a pacemaker detects an ALARM condition in the User's Heart, as described with reference to FIG. 4A, 4B, and 4C, then, as described with reference to FIG. 11 and based on the additional data from the Respiration Detector and the Galvanic Skin Detector, the Pace Signal Generator will commence pacing the User's Heart for a predetermined period of time.

There at least two types of pacemakers today that pace a user's heart based on the user's respiration, which are incorporated in a cardioverter defibrillator or a stand alone pacemaker. These are (1) transthoracic, or (2) impedance. A transthoracic pacemaker measures the expansion and contraction of the user's chest while inhaling and exhaling. An impedance pacemaker measures the electrical resistance in the air of the user's lungs while inhaling and exhaling. When the user inhales, the heart rate increases, and when the user exhales, the heart rate decreases.

Hereafter, the term pacemaker refers both to a stand alone pacemaker and a cardioverter defibrillator with a pacemaker, unless otherwise noted.

Therefor in order to program a cardioverter defibrillator with a pacemaker or a pacemaker, the patient user's Holter monitor records ECG RR together with respiratory and galvanic skin response baseline data as follows:

Daytime at rest for at least two hours

Nighttime at rest for at least two hours

Daytime exercise for at least 30 minutes sustained exercise

Then the Holter monitor ECG recordings should be edited deleting low variability episodes.

Then the ECG RR, the respiratory, and the galvanic skin response baseline data are stored in the pacemaker.

The stress formulas [1] through [17] are stored in the memory of the pacemaker.

When the pacemaker detects an ALARM, as defined in formulas [1] through [17], then the pacemaker will pace the user's heart using the user's appropriate variable heart rhythm data that occurred at the same time as the user's current respiratory state previously recorded, arid, if possible the user's galvanic skin response state, all as described above for a period of 10 minutes.

Then if the user's heart rhythm still generates ALARMs after 10 minutes of non-pacing, the pacemaker will again pace the user's heart for 100 minutes, again matching the user's heart rate variability with the user's respiratory state, and, if possible, the user's galvanic skin response state.

Then if a natural, variable sinus rhythm does not resume after 100 minutes of non pacing, then the pacemaker paces the heart for 1,000 minutes and so on in increasing powers of 10, or as programmed by the user's cardiologist.

If a cardioverter defibrillator with a pacemaker detects tachycardia, then the cardioverter defibrillator with a pacemaker will respond with a single extrastimulus burst, a double extrastimuli burst, or multiple extrastimuli bursts, as programmed.

Periodically, the user's recorded values for UV, AMo, and DX are down loaded to a PC from the user's pacemaker by telemetry for analysis of sympathetic and parasympathetic trends. All ALARM episodes, if any, as well a single extrastimulus burst, a double extrastimuli burst, or multiple extrastimuli bursts, in a cardioverter defibrillator with a pacemaker, if any, are date and time stamped.

If a Holter tape of the user's normal, variable heart rate is not available, then preferably the user is paced with a recording from a subject matched by age, race, sex, and physical condition, and also matched to the user's respiratory rates, and, if possible, to the user's galvanic skin response.

However, the user may be paced at a generated, histographically normal variable rate, matched to the user's respiratory rates, and the generated heart rate varied by the transthoracic or impedance pacemaker matching the user's respiratory rate simulating the wide saw tooth variability patterns of Time Intervals occurring naturally with reference to FIG. 50, and, if possible, to the user's galvanic skin response.

It will thus be seen that the objects set forth above, among those made apparent from the preceding descriptions: are efficiently attained and, since certain changes may be made in carrying out the above method in the apparatus set forth, without departing from the scope of the invention, it is intended that all matter contained in the above description or shown in the accompanying drawings and charts shall be interpreted as illustrative and not limiting in sense.

Having described our invention, what we claim as new and desire to secure by Letters Patent is:

1. A method of detecting abnormal heart rate variability comprising:
   A) recording a first subject's time interval between heart beats for a plurality of heart beats in a first Time Segment;
   B) identifying a characteristic of a histogram of said first subject's recorded time interval between heart beats, said characteristic including at least one of a Mode of said histogram, an Amplitude of said Mode (AMo), which is expressed as a percentage, and a difference between substantially a largest and substantially a smallest time interval between heart beats in said first Time Segment (DX);
   C) recording a second subject's time interval between heart beats for a plurality of heart beats in a second Time Segment;
   D) identifying a characteristic of a histogram of said second subject's recorded time interval between heart beats, said characteristic including at least one of a Mode of said histogram, an Amplitude of said Mode (AMo), which is expressed as a percentage, and a difference between substantially a largest and substantially a smallest instantaneous heart rate or RR interval in said second Time Segment (DX); and
   E) determining if said characteristic of said histogram of said second subject deviates from predetermined limits derived from said histogram of said first subject.

2. The method defined in claim 1, wherein said first and said second Time Segments include substantially no less than 50 to substantially no more than 300 heart beats and said intervals between heart beats are measured as a time between RR peaks.

3. A method of detecting abnormal heart rate variability, comprising:
   A) recording a subject's time interval between heart beats for a plurality of heart beats in a baseline Time Segment in which said subject's heart rate variability is normal
   B) recording said subject's time interval between heart beats for a plurality of heart beats in a current Time Segment; and
   C) identifying at least one characteristic of a baseline histogram, which is a histogram of said baseline Time Segment, and at least one characteristic of a current histogram, which is a histogram of said current Time Segment, if said characteristic of said current histogram differs by more than a predetermined percentage from said baseline histogram for a predetermined period of time, then said subject is deemed to be experiencing ectopic stress.

4. The method defined in claim 3, wherein said characteristic of said baseline and said current histograms includes at least one of a Mode, an Amplitude of a Mode (AMo), an Amplitude of a Median (AM), an Amplitude of a Mean, a difference between substantially a largest and substantially a smallest interval between heart beats in a Time Segment (DX), a ratio between AMo and DX, a flatness parameter, a Full Width at Half Maximum, and a standard deviation of said histogram.

5. The method defined in claim 3, wherein said characteristic of said baseline and said current histograms includes a number for a User's Value (UV), which is defined as follows:

$$UV = \sqrt{(0.5/DX)^2 + (AMo/10)^2}$$

where DX is a flatness parameter and AMo is an Amplitude of a Mode of the respective histogram, further comprising a step of generating a mixed sympathetic/parasympathetic alarm long term responsive to said UV for said current histogram differing from said UV for said baseline histogram by a predetermined amount for a first predetermined period of time, with no periods lasting a second predetermined period of time occurring during said first predetermined period of time in which said UV does not so differ.

6. The method defined in claim 3, wherein said characteristic of said baseline and said current histograms includes a number for a User's Value (UV), which is defined as follows:

$$UV = \sqrt{(0.5/DX)^2 + (AMo/10)^2}$$

where DX is a flatness parameter and AMo is an Amplitude of a Mode of the respective histograms, further comprising a step of generating a mixed sympathetic/parasympathetic alarm long term responsive to said UV for said current histogram differing from said UV for said baseline histogram by a predetermined amount for a first predetermined time period during a second predetermined time period that is longer than said first predetermined period of time.

7. The method defined in claim 3, further comprising the step of providing an indication responsive to said characteristic of said current histogram exceeding a predetermined limit.

8. The method defined in claim 7, further comprising the step of generating a sympathetic alarm if said characteristic of said current histogram differs from an associated characteristic of said baseline histogram by a predetermined amount in any of a first number of current Time Segments within any of a second number of contiguous Time Segments.

9. The method defined in claim 8, wherein said predetermined amount is at most 0.125 times said associated characteristic of said baseline histogram.

10. The method defined in claim 8, wherein said predetermined amount is approximately 0.425 times said associated characteristic for said baseline histogram.

11. The method defined in claim 7, wherein said characteristic of said current histogram is selected from the group consisting of UV, AMo, DX, and DX divided by one of M and AMo.

12. The method defined in claim 3, further comprising the step of generating a parasympathetic alarm signal if a flatness parameter (DX) of said current histogram is not less than approximately 0.05 in any of a first number of Time Segments within any of a second number of contiguous Time Segments.

13. The method defined in claim 3, further comprising the step of generating a parasympathetic alarm signal if said subject's AMo in said current histograms is not greater than approximately ten in any of a first number of Time Segments within any of a second number of contiguous Time Segments.

14. The method defined in claim 3, further comprising the step of generating a sympathetic caution-long term alarm signal if a difference between substantially a largest and substantially a smallest interval between heart beats (DX) in said current histogram is not greater than approximately 0.06 for a first period of time that is not less than approximately one hour.

15. The method defined in claim 3, further comprising the step of generating a caution-short term alarm signal if said subject's AMo and DX for a plurality of current histograms vary directly with each other for approximately one hour.

16. A method of indicating cardiac distress comprising:
   recording a user's baseline value for a characteristic selected from the group consisting of AMo and DX;
   recording a user's current value for a characteristic selected from the group consisting of AMo and DX; and
   generating an alarm responsive to said user's current value of said characteristic differing from said baseline value of said characteristic by a predetermined amount for a first period of time with no second periods of time occurring during said first period of time where said characteristic does not so differ.

17. The method defined in claim 16, wherein an AMo sympathetic alarm is generated responsive to said current value of AMo being greater than said baseline value of AMo.

18. The method defined in claim 16, wherein an AMo parasympathetic alarm is generated responsive to said current value of AMo being less than said baseline value of AMo.

19. A method of indicating cardiac distress comprising:
   recording a user's baseline value of;
   recording said user's current value of DX;
   generating a first alarm signal responsive to said user's current value of DX differing from said baseline value by a predetermined amount for a first period of time with no second periods of time occurring during said first period of time where said characteristic does not so differ, and
   recording said user's baseline value of AMo;
   recording said user's current value of AMo; and
   generating a second alarm signal responsive to said user's current value of AMo differing from said baseline value by a predetermined amount for a third period of time with no fourth periods of time occurring during said third period of time where said characteristic does not so differ.

20. The method defined in claim 19, further comprising the step of generating a mixed sympathetic/parasympathetic alarm long term responsive to said first and said second alarm signals being provided in an alternating manner for a fifth period of time with no sixth periods of time occurring during said fifth period of time where no first or second alarm signal occurs.

21. The method defined in claim 20, further comprising the step of generating a mixed sympathetic/parasympathetic alarm long term responsive to said first and said second alarm signals being provided in an alternating manner for a seventh period of time within an eighth time period that is longer than said seventh time period.

22. An apparatus comprising:
   A) means for recording a subject's time interval between heart beats for a plurality of heart beats;
   B) means for identifying at least one characteristic of a histogram of said recorded time intervals between heart beats and
   C) means for determining if said at least one characteristic of said histogram exceeds a predetermined limit.

23. The apparatus as defined in claim 22, further comprising a module adapted to be carried by said subject, said module containing said means for recording, said means for identifying at least one characteristic, and said means for determining if said at least one characteristic of said histogram exceeds a predetermined limit.

24. The apparatus as defined in claim 23, wherein said module further comprises:
   a) a motion sensor;
   b) means responsive to said motion sensor to distinguish between states of coma, sleep, wakefulness, and physical activity;
   c) a galvanic skin sensor; and
   d) means responsive to said galvanic skin sensor to determine whether said module is contacting said subject's skin.

25. The apparatus as defined in claim 22, wherein said characteristic of said histogram includes at least one of UV, AMo, DX, and DX divided by one of M and AMo.

26. The apparatus as defined in claim 22, wherein said predetermined limit is determined based on at least one of a characteristic of a baseline histogram, which is a histogram of said subject's time intervals between heart beats for a plurality of heart beats having normal variability, and a characteristic of a model histogram, which is a histogram of time intervals between heart beats for a plurality of heart beats in an individual having at least one characteristic approximating an associated characteristic of said subject.

27. The apparatus as defined in claim 22, further comprising at least one of the following:
   means for transmitting data output by at least one of said means for recording, said means for identifying at least one characteristic of said histogram, and said means for determining if said at least one characteristic of said histogram exceeds said predetermined limit; and
   means for displaying in a human perceivable format data output by at least one of said means for recording, said means for identifying at least one characteristic of said histogram, and said means for determining if said at least one characteristic of said histogram exceeds said predetermined limit.

28. The apparatus as defined in claim 22, further comprising means for transmitting first data output by at least one of said means for recording, said means for identifying at least one characteristic of said histogram, and said means for determining if said at least one characteristic of said histogram exceeds said predetermined limit;
   a base station adapted to receive said first data, wherein said base station includes means for outputting, in a human perceivable format, at least one of said first data and information based on said first data.

29. A method of detecting abnormal heart rate variability, comprising:
   recording a subject's time interval between heart beats for a plurality of heart beats;

identifying at least one characteristic of a histogram of said recorded time intervals between heart beats; and determining if at least one characteristic of said histogram exceeds a predetermined limit.

30. The method defined in claim 29, further comprising:

distinguishing, based on motion of said subject, between states of coma, sleep, wakefulness, and physical activity; and determining whether said step of recording a subject's time interval between heart beats is taking place properly based on a determination of whether sensors for detecting heart beats are contacting said subjects skin.

31. The method defined in claim 30, wherein said step of identifying a characteristic of said histogram includes identifying at least one of UV, AMo, DX, and DX divided by one of M and AMo.

32. The apparatus as defined in claim 30, wherein said step of determining if at least one characteristic of said histogram exceeds a predetermined limit includes setting said predetermined limit as at least one of a characteristic of a baseline histogram, which is a histogram of said subject's time intervals between heart beats for a plurality of heart beats having normal variability, and a characteristic of a model histogram, which is a histogram of time intervals between heart beats for a plurality of heart beats in an individual having at least one characteristic approximating an associated characteristic of said subject.

33. The apparatus as defined in claim 30, further comprising at least one of the following steps:

transmitting data produced in at least one of said steps of recording, identifying at least one characteristic of said histogram, and determining if said at least one characteristic of said histogram exceeds said predetermined limit; and displaying in a human perceivable format data produced by at least one of said steps of recording, identifying at least one characteristic of said histogram, and determining if said at least one characteristic of said histogram exceeds said predetermined limit.

34. The apparatus as defined in claim 33, further comprising transmitting to a base station first data produced in least one of said steps of recording, identifying at least one characteristic of said histogram, and determining if said at least one characteristic of said histogram exceeds said predetermined limit; and outputting in a human perceivable format at least one of said first data and information produced based on said first data.

* * * * *